US008900847B2

(12) United States Patent
Clark et al.

(10) Patent No.: US 8,900,847 B2
(45) Date of Patent: *Dec. 2, 2014

(54) POLYNUCLEOTIDES ENCODING RECOMBINANT C1 BETA-GLUCOSIDASE FOR PRODUCTION OF SUGARS FROM CELLULOSIC BIOMASS

(75) Inventors: Louis Clark, San Francisco, CA (US);
Dipnath Baidyaroy, Fremont, CA (US);
Lorand Szabo, Budapest (HU)

(73) Assignee: Codexis, Inc., Redwood City, CA (US)

( * ) Notice: Subject to any disclaimer, the term of this patent is extended or adjusted under 35 U.S.C. 154(b) by 137 days.

This patent is subject to a terminal disclaimer.

(21) Appl. No.: 13/496,368

(22) PCT Filed: Sep. 30, 2010

(86) PCT No.: PCT/US2010/050982
§ 371 (c)(1),
(2), (4) Date: Apr. 12, 2012

(87) PCT Pub. No.: WO2011/041594
PCT Pub. Date: Apr. 7, 2011

(65) Prior Publication Data
US 2012/0190076 A1    Jul. 26, 2012

Related U.S. Application Data

(60) Provisional application No. 61/247,379, filed on Sep. 30, 2009.

(51) Int. Cl.
| *C07H 21/00* | (2006.01) |
| *C12N 15/00* | (2006.01) |
| *C12P 21/00* | (2006.01) |
| *C12N 1/21* | (2006.01) |
| *C12N 5/10* | (2006.01) |
| *C12P 19/14* | (2006.01) |
| *C12N 9/42* | (2006.01) |
| *C12N 9/24* | (2006.01) |

(52) U.S. Cl.
CPC ............ *C12P 19/14* (2013.01); *C12N 9/2445* (2013.01); *C12Y 302/01021* (2013.01)
USPC .... 435/200; 435/320.1; 435/69.1; 435/252.3; 435/325; 536/23.2

(58) Field of Classification Search
CPC ....... C12P 19/14; C12P 19/02; C12N 9/2445; C12Y 302/01021; C07K 14/37
USPC ................. 435/320.1, 69.1, 252.3, 325, 200
See application file for complete search history.

(56) References Cited

U.S. PATENT DOCUMENTS

| 4,486,553 A | 12/1984 | Wesch |
| 4,683,202 A | 7/1987 | Mullis |
| 5,426,039 A | 6/1995 | Wallace et al. |
| 5,648,263 A | 7/1997 | Schulein et al. |
| 5,811,381 A | 9/1998 | Emalfarb et al. |
| 6,015,707 A | 1/2000 | Emalfarb et al. |
| 6,117,679 A | 9/2000 | Stemmer |
| 6,376,246 B1 | 4/2002 | Crameri et al. |
| 6,573,086 B1 | 6/2003 | Emalfarb et al. |
| 6,586,182 B1 | 7/2003 | Patten et al. |
| 7,244,605 B2 | 7/2007 | Harris et al. |
| 7,696,411 B2 | 4/2010 | Sticklen et al. |
| 7,883,872 B2 | 2/2011 | Gusakov et al. |
| 7,906,309 B2 | 3/2011 | Emalfarb et al. |
| 8,017,361 B2 | 9/2011 | Scott et al. |
| 8,017,373 B2 | 9/2011 | Hill et al. |
| 2003/0187243 A1* | 10/2003 | Emalfarb et al. ............ 536/23.2 |
| 2007/0238155 A1 | 10/2007 | Gusakov et al. |
| 2008/0194005 A1 | 8/2008 | Emalfarb et al. |
| 2008/0199908 A1 | 8/2008 | Smith et al. |
| 2008/0220990 A1 | 9/2008 | Fox |
| 2009/0099079 A1 | 4/2009 | Emalfarb et al. |
| 2009/0209009 A1 | 8/2009 | Tolan et al. |
| 2009/0280105 A1 | 11/2009 | Gusakov et al. |
| 2009/0312196 A1 | 12/2009 | Colbeck et al. |

FOREIGN PATENT DOCUMENTS

| EP | 0137280 B1 | 3/1992 |
| WO | 98/15633 A1 | 4/1998 |
| WO | 01/79507 A2 | 10/2001 |
| WO | 2004/048592 A2 | 6/2004 |
| WO | 2008/008070 A2 | 1/2008 |
| WO | 2008/073914 A2 | 6/2008 |

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Gusakov, A.L., et al., "N-Glycosylation in Chrysosporium lucknowense Enzymes," Carbohydrate Research, 343:48-55 [2008].
Adams, S.P., et al., "Hindered dialkylamino nucleoside phosphite reagents in the synthesis of two DNA 51-mers," J. Am. Chem. Soc., 105:661 (1983).
Altschul, S.F., et al., "Basic Local Alignment Search Tool," J. Mol. Biol., 215: 403-410 [1990].
Altschul, S.F., et al., "Gapped BLAST and PSI-BLAST: a new generation of protein database search programs," Nucleic Acids Res., 25(17):3389-3402 (1997).

(Continued)

*Primary Examiner* — Delia Ramirez
(74) *Attorney, Agent, or Firm* — Codexis, Inc.

(57) ABSTRACT

The invention relates to expression of a recombinant C1 β-glucosidase. The invention also provides methods for producing a fermentable sugar from cellobiose by contacting celiobiose with a recombinant host cell comprising a polynucleotide sequence encoding C1 β-glucosidase, operably linked to heterologous promoter, under conditions in which β-glucosidase is expressed and secreted by the cell and the cellobiose is enzymatically converted by said β-glucosidase to glucose. Methods of the invention may be used for conversion of a biomass substrate to a fermentable sugar, and ultimately to ethanol or other biofuel.

15 Claims, 15 Drawing Sheets

(56) References Cited

OTHER PUBLICATIONS

Arnheim, N., et al., "Polymerase Chain Reaction," C&EN, pp. 36-47 (1990).
Barringer, K.J., et al., "Blunt-end and single-strand ligations by Escherichia coli ligase: influence on an in vitro amplification scheme," Gene, 89:117-122 (1990).
Beaucage, S.L., et al., "Deoxynucleoside phosphoamidites-A new class of key intermediates for deoxypolynucleotide synthesis," Tetrahedron Letters, 22(20):1859-62 (1981).
Bendtsen, J.D., et al., "Improved prediction of signal peptides: SignalP 3.0," J. Mol. Biol.,. 340(4):783-95 (2004).
Blaiseau, P-L., et al., "Primary structure of a chitinase-encoding gene (chi1) from the filamentous fungus Aphanocladium album: similarity to bacterial chitinases," Gene, 120(2):243-248 (1992).
Boel, E., et al., "Two different types of intervening sequences in the glucoamylase gene from *Aspergillus niger*," Embo J., 3(7):1581-1585 (1984).
Breves, R., et al., "Genes encoding two different beta-gludosidases of *Thermoa naerobacter brockii* are clustered in a common operon," Appl. Environ. Microbiology, 63(10):3902-3910 [1997].
Brigham, J.S., et al., "Hemicellulases: Diversity and Applications," in Handbook on Bioethanol (C. Wyman ed.) pp. 119-141, Taylor and Francis, Washington DC, (1995).
Caruthers, M.H., et al., "Chemical Synthesis and Biological Studies on Mutated Gene-control Regions," Cold Spring Harbor Symp. Quant. Biol., 47:411-418 (1982).
Case, M.E. et al., "Efficient transformation of *Neurospora crassa* by utilizing hybrid plasmid DNA," Proc. Natl. Acad. Sci. USA, 76(10):5259-5263 (1979).
Garg. A.K., "An addition to the genus *Chrysosporium* corda," Mycopathologia, 30(3-4):221-224 (1966).
Guatelli, J.C., et al., "Isothermal, in vitro amplification of nucleic acids by a multienzyme reaction modeled after retroviral replication," Proc. Natl. Acad. Sci. USA, 87:1874-1878 (1990).
Heanut, A., et al., "Analysis and predictions from *Escherichia coli* sequences, or *E. coli* in silico," in *Escherichia coli* and *Salmonella*, ASM Pres, Washington D.C., pp. 2047-2066 (1987).
Henriksen, A.L.S., et al., "Study of the glucoamylase promoter in *Aspergilllus niger* using green fluorescent protein," Microbiol., 145:729-34 [1999].
Johnstone, I.L., et al., "Cloning an *Aspergillus nidulans* developmental gene by transformation," Embo J., 4(5):1307-1311 (1985).
Karlin, S., et al., "Applications and statistics for multiple high-scoring segments in molecular sequences," Proc. Natl. Acad. Sci. USA, 90:5873-5787 (1993).
Kelly, J.M., et al., "Transformation of *Asoergillus niger* by the amdS gene of *Aspergillus nidulans*," Embo J., 4(2):475-479 (1985).
Kinsey, J.A., et al., "Transformation of *Neurospora crassa* with the Cloned am (Glutamate Dehydrogenase) Gene", Molecular and Cellular Biology, 4:117-122 (1984).
Kwoh, D.Y., et al., "Transcription-based amplification system and detection of amplified human immunodeficiency virus type 1 with a bead-based sandwich hybridization format," Proc. Natl. Acad. Sci. USA, 86:1173-1177 (1989).
Ladisch, M.R., et al., "Process considerations in the enzymatic hydrolysis of biomass," Enzyme Microb. Technol., 5:82 (1983).
Landegren, U., et al., "A Ligase-Mediated Gene Detection Technique," Science, 241:1077-1080 (1988).
Limon, C., et al., "Primary structure and expression pattern of the 33-kDa chitinase gene from the nucoparasitic fungus *Trichocherma harzianum*," Curr. Genet., 28:478-83 [1995].
Lomeli, H., et al., "Quantitative Assays Based on the Use of Replicatable Hybridization Probes," J. Clin. Chem, 35(9): 1826-1831 (1989).
Li, M.Z., et al., "Harnessing homologous recombination in vitro to generate recombinant DNA via SLIC," Nature Methods, 4:251-56 (2007).
Mase, T., et al., "Purification, characterization, and a potential application of beta-gludosidase from *Asperfillus pulverulentus* YM-80," J. Appl. Glycosci., 51:211-216 (2004).

Matthes, H.W.D., et al., "Simultaneous rapid chemical synthesis of over one hundred oligonucleotides on a microscale," Embo J., 3(4):801-05 (1984).
McInerney, J.O., "GCUA: general codon usage analysis," Bioinformatics, 14(4):372-73, 1998.
Nakamura, Y., et al., "Codon usage tabulated from international DNA sequence databases: status for the year 2000," Nucl. Acids Res., 28:292, 2000.
Nunberg, J.H., et al., "Molecular Cloning and Characterization of the Glucoamylase Gene of *Aspergillus awamori*," Mol. Cell Biol., 4(11):2306-2315 (1984).
Porath, J., "Immobilized metal ion affinity chromatography," Protein Expression and Purification, 3:263-281 (1992).
Punt, P.J. et al., "Intracellular and extracellular production of proteins in *Aspergillus* under the control of expression signals of the highly expressed *Aspergillus nidulans* gpdA gene," J. Biotechnol., 17:19-33 [1991].
Ricciardelli, C., et al., "Development and characterization of primary cultures of smooth muscle cells from the fibromuscular stroma of the guinea pig prostate," In vitro Cell Dev. Biol., 25:1016-1024 (1989).
Robert, "Amplification of the nucleic acid sequence: The choices multiply," The Journal of NIH Research, 3:81-94 (1991).
Romanos, M.A., et al., "Foreign gene expression in yeast: a review," Yeast 8:423-488 [1992].
Sheir-Neiss, G., et al., "Characterization of the secreted cellulases of *Trichoderma reesei* wild type and mutants during controlled fermentations," Appl. Microbiol. Biotechnol., 20:46-53 (1984).
Simonen, M., et al., "Protein Secretion in *Bacillus* Species," Microbiological Reviews, 57:109-137 (1993).
Sooknanan, R., et al., "NASBRA: A detection and amplification system uniquely suited for RNA," Biotechnology, 13:563-564 (1995).
Stanke, M., et al., "AUGUSTUS: ab initio prediction of alternative transcripts," Nucleic Acids Res., 34(Web Server issue):W435-9 (2006).
Stenico, M., et al., "Codon usage in *Caenorhabditis elegans*: delineation of translational selection and mutational biases," Nucl. Acids Res., 22(13):2437-46, 1994.
Ter-Hovhannisyan, V., et al., "Gene prediction in novel fungal genomes using an ab initio algorithm with unsupervised training," Genome Res., 18:1979-90 (2008).
Tilburn, J., et al., "Transformation by integration in *Asperfillus nidulans*," Gene, 26:205-221 (1982).
Tiwari, S.,et al., "Prediction of probable genes by Fourier analysis of genomic sequences," Comput. Appl. Biosci., 13(3):263-270 (1997).
Uberbacher, E.C., et al., "Discovering and Understanding Genes in Human DNA Sequence Using GRAIL," Meth. Enzymol., 266:259-281 (1996).
Van Brunt, J., "Amplifying Genes: PCR and its alternatives," Biotechnology, 8:291-294 (1990).
Viikari, L., et al., "Thermostable enzymes in lignocellulose hydrolysis," Adv. Biochem. Eng. Biotechnol., 108:121-45 [2007].
Wada, K., et al., "Codon usage tabulated from the GenBank genetic sequence data," Nucl. Acids Res., 20:2111-2118 (1992).
Wilson, I.A., et al., "The structure of an antigenic determinant in a protein," Cell, 37:767-78 (1984).
Wright, A., et al., "Diverse Plasmid DNA Vectors by Directed Molecular Evolution of *Cytomegalovirus* Promoters," Hum. Gene Ther., 16:881-892 [2005].
Wright, F., "The 'effective number of codons' used in a gene," Gene, 87:23-29 (1990).
Wu, D.Y., et al., "The Ligation Amplification Reaction (LAR)-Amplification of Specific DNA Sequences Using Sequential Rounds of Template-Dependent Ligation," Genomics, 4:560 (1989).
Yanai, T., et al., "Isolation and Properties of Beta-Glucosidase Produced by *Debaryomyces hansenii* and Its Application in Winemaking," Am. J. Enol. Eitic., 50(3):231-235 (1999).
Yelton, M.M., et al., "Transformation of *Aspergillus nidulans* by using a trpC plasmid," Proc. Natl. Acad. Sci. USA, 81:1470-1474 (1984).
Zhu, T., et al., "Construction of two Gateway vectors for gene expression in fungi," Plasmid, 62:128-33 [2009].

\* cited by examiner

C1 β-glucosidase Polynucleotides

The upper sequence is genomic DNA (SEQ ID NO:1).
The lower sequence is cDNA (SEQ ID NO:2).
Gaps in the lower sequence show position of introns.

```
ATGAAGGCTGCTGCGCTTTCCTGCCTCTTCGGCAGTACCCTTGCCGTTGCAGGCGCCATTGAATCGAGAAAGGTATGGAC
ATGAAGGCTGCTGCGCTTTCCTGCCTCTTCGGCAGTACCCTTGCCGTTGCAGGCGCCATTGAATCGAGAA----------
12345678901234567890123456789012345678901234567890123456789012345678901234567890
         1         2         3         4         5         6         7         8

GGGCTTTCGTCAAAGACTCGCTCCCCGATCAACTTCCCCTTTCATCCAGACCACCCCAACCCTCCCAGTCCTGCTTCGAG
----------------------------------------------------------------------------GAG
12345678901234567890123456789012345678901234567890123456789012345678901234567890
         9        10        11        12        13        14        15

CACGATCTCTTCGGGCAGCACCCCACCCACTCAGATTAGCGGCGACACCGTTGACTGTTGCAATCCGCAATCGA
CACGATCTCTTCGGGCAGCACCCCACCCACTCAGATTAGCGGCGACACCGTTGACTGTTGCAATCCGCAATCGA
12345678901234567890123456789012345678901234567890123456789012345678901234567890
        17        18        19        20        21        22        23

CATGCAACTTCCAGCCGCCAATGGCTGCTCACGCTTCCCGCGAAAGCCTCACTTGCTGACAATCATCGTCAGGTTC
CATGCAACTTCCAGCCGCCAATGGCTGCTCACGCTTCCCGCGAAAGCCTCACTTGCTGACAATCATCGTCAGGTTC------AGGTTC
12345678901234567890123456789012345678901234567890123456789012345678901234567890
        25        26        27        28        29        30        31

ACCAGAAGCCCCTCGCGAGATCTGAACCTTTTTACCCGTCGCCATGGATGAATCCCAACGCCGCTGGGCGGAGCC
ACCAGAAGCCCCTCGCGAGATCTGAACCTTTTTACCCGTCGCCATGGATGAATCCCAACGCCGCTGGGCGGAGCC
12345678901234567890123456789012345678901234567890123456789012345678901234567890
        33        34        35        36        37        38        39

TATGCCCAGGCCAAGTCCTTTGTCTCCCAAATGACTCTGCTAGAGAAGGTCAACTTGACCACGGGAGTCGGGTAAGTTTT
```

FIG. 1A

```
TATGCCCAGGCCAAGTCCTCTTTGTCTCCCAAATGACTCTGCTAGAGAAGGTCAACTTGACCACGGGAGTCG----------
1234567890123456789012345678901234567890123456789012345678901234567890
0           41         42         43         44         45         46         47

GTCATTTTGTCCAGGTAACATGCAAATGGTTCTGCTAACAATAACTTACCGTAGCTGGGGGGCTGAGCAGTGCTGTCGGCC
----------------------------------------------------------GCTGGGGGGCTGAGCAGTGCTGTCGGCC
1234567890123456789012345678901234567890123456789012345678901234567890
8           49         50         51         52         53         54         55

AAGTGGGCGCGATCCCTCGCCTTGGACTTCGCAGTCTGTGCATGCATGACTCCCCTCTCGGCATCCGAGGAGCCGACTAC
AAGTGGGCGCGATCCCTCGCCTTGGACTTCGCAGTCTGTGCATGCATGACTCCCCTCTCGGCATCCGAGGAGCCGACTAC
1234567890123456789012345678901234567890123456789012345678901234567890
6           57         58         59         60         61         62         63

AACTCAGCGTTCCCCTCTGGCCAGACCGTTGCTGCTACCTGGGATCGCGGTCTGATGTACCGTCGCGGCTACGCAATGGG
AACTCAGCGTTCCCCTCTGGCCAGACCGTTGCTGCTACCTGGGATCGCGGTCTGATGTACCGTCGCGGCTACGCAATGGG
1234567890123456789012345678901234567890123456789012345678901234567890
4           65         66         67         68         69         70         71

CCAGGAGGCCAAAGGCAAGGGCATCAATGTCCTTCTCGGACCAGTCGCCGGCCCCCCCTTGGCCGCCATGCCCGAGGCGGTC
CCAGGAGGCCAAAGGCAAGGGCATCAATGTCCTTCTCGGACCAGTCGCCGGCCCCCCCTTGGCCGCCATGCCCGAGGCGGTC
1234567890123456789012345678901234567890123456789012345678901234567890
2           73         74         75         76         77         78         79

GTAACTGGGAAGGCTTCGCTCCGAAGCACTTTATTGGAAACGAGCAGGGTGAGTAGTCAAAGACGGCCGTCTCGGACCCGCGGCATTCAGGATGCT
GTAACTGGGAAGGCTTCGCTCCGAAGCACTTTATTGGAAACGAGCAG----------------------------------
1234567890123456789012345678901234567890123456789012345678901234567890
0           81         82         83         84         85         86         87

GGCGTCATCGCTTGTGCGAAGCACTTTATTGGAAACGAGCAGGGTGAGTAGTCAAAGACGGCCGTCTCGGACCCGCGGC
GGCGTCATCGCTTGTGCGAAGCACTTTATTGGAAACGAGCAG-----------------------------------
1234567890123456789012345678901234567890123456789012345678901234567890
8           89         90         91         92         93         94         95
```

FIG. 1B

```
TTCAAGCTGCTGACTCTGCTGCAGAGCACTTCAGACAGGTGCCAGAAGCCCAGGGATACGGTTACAACATCAGCGAAACC
-------------------GAGCACTTCAGACAGGTGCCAGAAGCCCAGGGATACGGTTACAACATCAGCGAAACC
123456789012345678901234567890123456789012345678901234567890
         97              98              99             100             101             102             103
                                                                                                         1

CTCTCCTCCAACATTGACGACAAGACCATGCACGAGCTCTACCTTTGCCGATGCCGTTTGCCGGGCCGGCGTCGG
CTCTCCTCCAACATTGACGACAAGACCATGCACGAGCTCTACCTTTGCCGATGCCGTTTGCCGGGCCGGCGTCGG
123456789012345678901234567890123456789012345678901234567890
        105             106             107             108             109             110             111
 04                                                                                                      1

CTCTGTCATGTGCTCGTACCAGCAGGTCAACAACTCGTACGCCCTGCCAGAACTCGAAGCTGCTGAACGACCTCCTCAAGA
CTCTGTCATGTGCTCGTACCAGCAGGTCAACAACTCGTACGCCCTGCCAGAACTCGAAGCTGCTGAACGACCTCCTCAAGA
123456789012345678901234567890123456789012345678901234567890
        113             114             115             116             117             118             119
 12                                                                                                      1

ACGAGCTTGGGTTTCAGGGCTTCGTCATGAGCGACTGGCAGGCACAGCACACTGGCGCAGCAAGCGCCGTGGCTGGTCTC
ACGAGCTTGGGTTTCAGGGCTTCGTCATGAGCGACTGGCAGGCACAGCACACTGGCGCAGCAAGCGCCGTGGCTGGTCTC
123456789012345678901234567890123456789012345678901234567890
        121             122             123             124             125             126             127
 20                                                                                                      1

GATATGTCCATGCCGGGCGACACCCAGTTCAACACTGGCCGTCAGTTTCTGGGGCGCCAATCTCACCCTCGCCGTCCTCAA
GATATGTCCATGCCGGGCGACACCCAGTTCAACACTGGCCGTCAGTTTCTGGGGCGCCAATCTCACCCTCGCCGTCCTCAA
123456789012345678901234567890123456789012345678901234567890
        129             130             131             132             133             134             135
 28                                                                                                      1

CGGCACAGTCCCTGCCTACCGTCTCGACGACATGGCCATGCATGGCCGCCCTCTTCAAGGTCACCAAGACCACCG
CGGCACAGTCCCTGCCTACCGTCTCGACGACATGGCCATGCATGGCCGCCCTCTTCAAGGTCACCAAGACCACCG
123456789012345678901234567890123456789012345678901234567890
        137             138             139             140             141             142             143
 36                                                                                                      1

ACCTGGAACCGATCAACTTCCCTTCTGGACCGACGACACTTATGGCCCGATCCACTGGGCCGCCAAGCAGGGCTACCAG
ACCTGGAACCGATCAACTTCCCTTCTGGACCGACGACACTTATGGCCCGATCCACTGGGCCGCCAAGCAGGGCTACCAG
```

GAGATTAATTCCCACGTTGACGTTCCGCGCCGACCACGGCCAACCTCATCCGGGAGATTGCCGCCAAGGGTACGGTGCTGCT
 52             153               154               155               156               157               158               159      1

GAAGAATACCGGCTCTCTACCCCTGAACAAGCCAAAGTTCGTGGCCGTCATCGGCGAGGATGCTGGGTCGAGCCCCAACG
 60             161               162               163               164               165               166               167      1

GGCCCAACGGCTGCAGCGACCGCGGCTGTAACGAAGGCACGCTCGCCATGGGCTGGGATCCGGCACAGCCAACTATCCG
 68             169               170               171               172               173               174               175      1

TACCTCGTTTCCCCGACGCGCCGGCCGCGCTCCAGGCCCGGCCATCCAGGACGGCACGAGGTACGAGAGCGTCCTGTCCAACTA
 76             177               178               179               180               181               182               183      1

CGCCGAGGAAAAGACAAAGGCTCTGGTTCTCGCAGGCCAGGCCAATGCAACCGCCATCGTCTTCGTCAATGCCAATCAGGCGAGG
 84             185               186               187               188               189               190               191      1

GCTACATCAACGTGGACGGTAACGAGGGGCGACCGTAAGAGGGGTGACCTCTCTGGAACAACGGTGATACTCTGGTCAAGAAC
 92             193               194               195               196               197               198               199      2

GTCTCGAGCTGGTGCAGCAACACCATCGTCGTCATCGTCATCCACTCGGTCGGCCCCGTCCTCCTGACCGATTGGTACGACAACCC
```

FIG. 1D

```
GTCTCGAGCTGGTGCAGCAACACCATCGTCGTCATCCACTCGGTCGGCCCGTCCTCTGACCGATTGGTACGACAACCC
123456789012345678901234567890123456789012345678901234567890123456789012345678902
00            201           202           203           204           205           206           207

CAACATCACGGCCATTCTCTGGGCTGGTCTTCCGGGCCAGGAGTCGGGCAACTCCATCACCGACGTGCTTTACGGCAAGG
123456789012345678901234567890123456789012345678901234567890123456789012345678902
08            209           210           211           212           213           214           215

TCAACCCCGCCGCCCGCTCGCCCTTCACTTGGGGCAAGACCCGCGAAAGCTATGGCGGACGTCCTGTACAAGCCGAAT
123456789012345678901234567890123456789012345678901234567890123456789012345678902
16            217           218           219           220           221           222           223

AATGGCAATGTGCGCCCCAACAGGACTTCACCGAGGGCGTCTCTTCATCGACTACCGCTACTTCGACAAGGTTGACGATGA
123456789012345678901234567890123456789012345678901234567890123456789012345678902
24            225           226           227           228           229           230           231

CTCGGTCATCTACGAGTTCGGCCACGGCCTGAGCTACACACCTTCGAGTACAGCAACATCCGCGTCGTCAAGTCCAACG
123456789012345678901234567890123456789012345678901234567890123456789012345678902
32            233           234           235           236           237           238           239

TCAGCGAGTACCGGCCCACGGCCCACGGGCACCAGGCCCCCGACGTTTGGCAACTTCTCCACCGACCTCGAGGACTAT
123456789012345678901234567890123456789012345678901234567890123456789012345678902
40            241           242           243           244           245           246           247

CTCTTCCCCAAGGACGAGTTCCCCTACCTCTACATCTACCCGTACCTCAACACGACCCCCGGAGGGCCTC
123456789012345678901234567890123456789012345678901234567890123456789012345678902
48            249           250           251           252           253           254           255
```

FIG. 1E

```
GGCCGATCCCCACTACGGCCAGAGACCGCCGAGGAGTTCCTCCCGCCCCAGCCCCAGCCGATGACGACCCCAGCCGCTCCTCC
GGCCGATCCCCACTACGGCCAGAGACCGCCGAGGAGTTCCTCCTCCCGCCCCAGCCCCAGCCGATGACGACCCCAGCCGCTCCTCC
GGCCGATCCCCACTACGGCCAGAGACCGCCGAGGAGTTCCTCCTCCCGCCCCAGCCCCAGCCGATGACGACCCCAGCCGCTCCTCC
1234567890123456789012345678901234567890123456789012345678901234567890123456789012
56         257         258         259         260         261         262         263 2

GGTCCTCGGGCGGAAACTCCCCCGGCGGCCAACCGCCAGCTGTACGACATTGTCTACACAATCACGGCCGACATCACGAAT
GGTCCTCGGGCGGAAACTCCCCCGGCGGCCAACCGCCAGCTGTACGACATTGTCTACACAATCACGGCCGACATCACGAAT
GGTCCTCGGGCGGAAACTCCCCCGGCGGCCAACCGCCAGCTGTACGACATTGTCTACACAATCACGGCCGACATCACGAAT
1234567890123456789012345678901234567890123456789012345678901234567890123456789012
64         265         266         267         268         269         270         271 2

ACGGGCTCCGTTGTAGGCGAGGAGGTACCGCAGCTCTCGCTCTACGTCTCGCTGGGCGGTCCCGAGGATCCCAAGGTGCAGCTGCG
ACGGGCTCCGTTGTAGGCGAGGAGGTACCGCAGCTCTCGCTCTACGTCTCGCTGGGCGGTCCCGAGGATCCCAAGGTGCAGCTGCG
ACGGGCTCCGTTGTAGGCGAGGAGGTACCGCAGCTCTCGCTCTACGTCTCGCTGGGCGGTCCCGAGGATCCCAAGGTGCAGCTGCG
1234567890123456789012345678901234567890123456789012345678901234567890123456789012
72         273         274         275         276         277         278         279 2

CGACTTTGACAGGATGCGGATCGAACCCGGCGAGACGAGGCAGTTCACCGGCCGCCTGCCGCCAGAGATCTGAGCAACT
CGACTTTGACAGGATGCGGATCGAACCCGGCGAGACGAGGCAGTTCACCGGCCGCCTGCCGCCAGAGATCTGAGCAACT
CGACTTTGACAGGATGCGGATCGAACCCGGCGAGACGAGGCAGTTCACCGGCCGCCTGCCGCCAGAGATCTGAGCAACT
1234567890123456789012345678901234567890123456789012345678901234567890123456789012
80         281         282         283         284         285         286         287 2

GGGACGTCACGGTGCAGGACTGGGTCAGGACTGGGTCATCAGCAGGTATCCCAAGACGGCCATATGTTGGGAGGAGCAGCCGGAAGTTGGAT
GGGACGTCACGGTGCAGGACTGGGTCATCAGCAGGTATCCCAAGACGGCCATATGTTGGGAGGAGCAGCCGGAAGTTGGAT
GGGACGTCACGGTGCAGGACTGGGTCATCAGCAGGTATCCCAAGACGGCCATATGTTGGGAGGAGCAGCCGGAAGTTGGAT
1234567890123456789012345678901234567890123456789012345678901234567890123456789012
88         289         290         291         292         293         294         295 2

CTCAAGATTGAGCTTCCTTGA
CTCAAGATTGAGCTTCCTTGA
123456789012
96         297 298
```

FIG. 1F

BGL1 cDNA and protein sequences (SEQ ID NOS: 2 and 4)

```
ATGAAGGCTGCTGCGCTTTCCTGCCTCTTCGGCAGTACCCTTGCCGTTGCAGGCGCCATTGAATCGAGAAAGGTTCACCAGAAGCCCCTC
 M  K  A  A  A  L  S  C  L  F  G  S  T  L  A  V  A  G  A  I  E  S  R  K  V  H  Q  K  P  L
 1234567890123456789012345678901234567890123456789012345678901234567890123456789012345678901234567890
          1         2         3         4         5         6         7         8         9

GCGAGATCTGAACCTTTTTTACCCGTCGCCATGGATGAATCCCAACGCCGGCTGGGCGGAGCCTATGCCCAGGCCAAGTCCTTTGTC
 A  R  S  E  P  F  Y  P  S  P  W  M  N  P  N  A  D  G  W  A  E  A  Y  A  Q  A  K  S  F  V
 1234567890123456789012345678901234567890123456789012345678901234567890123456789012345678901234567890
         10        11        12        13        14        15        16        17

TCCCAAATGACTCTGCTAGAGAAGGTCAACTTGACCACGGGAGTCGGCTGGGGGCTGAGCAGTGCGTCGGCCAAGTGGGCGCGATCCCT
 S  Q  M  T  L  L  E  K  V  N  L  T  T  G  V  G  W  G  A  E  Q  C  V  G  Q  V  G  A  I  P
 1234567890123456789012345678901234567890123456789012345678901234567890123456789012345678901234567890
 8        19        20        21        22        23        24        25        26        2

CGGCCTTGGGACTTCGCAGTCTGTGCATGCATGACTCCCCTCTCGGCATCCGAGGAGCCGACTACAACTCAGCGTTCCCCTCTGGCCAGACC
 R  L  G  L  R  S  L  C  M  H  D  S  P  L  G  I  R  G  A  D  Y  N  S  A  F  P  S  G  Q  T
 1234567890123456789012345678901234567890123456789012345678901234567890123456789012345678901234567890
 7        28        29        30        31        32        33        34        35        3

GTTGCTGCTACCTGGGATCGCGGTCTGATGTACCGTCGCGGCTACGCAATGGGCCAGGAGCCAAGGCATCAATGTCCTTCTC
 V  A  A  T  W  D  R  G  L  M  Y  R  R  G  Y  A  M  G  Q  E  A  K  G  I  N  V  L  L
 1234567890123456789012345678901234567890123456789012345678901234567890123456789012345678901234567890
 6        37        38        39        40        41        42        43        44        4

GGACCAGTCGCCGGCCCCTTGGCCGCAGCATTCAGGAGCGCGTAACTGGGAAGGCTTCGCTCCGGATCCCGTCCTTACCGGCATCGGC
 G  P  V  A  G  P  L  G  R  M  P  E  G  G  R  N  W  E  G  F  A  P  D  P  V  L  T  G  I  G
 1234567890123456789012345678901234567890123456789012345678901234567890123456789012345678901234567890
 5        46        47        48        49        50        51        52        53

ATGTCCGAGACGATCAAGGGCATTCAGGATGCTGGCGTCATCGCTTGTGCGAAGCACTTTATTGGAAACGAGCAGGAGCACTTCAGACAG
 M  S  E  T  I  K  G  I  Q  D  A  G  V  I  A  C  A  K  H  F  I  G  N  E  Q  E  H  F  R  Q
 1234567890123456789012345678901234567890123456789012345678901234567890123456789012345678901234567890
 4        55        56        57        58        59        60        61        62        6
```

FIG. 2A

```
GTGCCAGAAGCCCAGGGATACGGTTACAACATCAGCGAAACCCTCTCCTCCAACATTGACGACAAGACCATGCACGAGCTCTACCTTTGG
 V  P  E  A  Q  G  Y  G  Y  N  I  S  E  T  L  S  S  N  I  D  D  K  T  M  H  E  L  Y  L  W
123456789012345678901234567890123456789012345678901234567890123456789012345678901234567890
        64            65            66            67            68            69           70            71       7
CCGTTTGCCGATGCCGTCCGGGCCGGCGTCGCCGGCCTCTGTCTGTGTCATGTGTTCGTACCAGCAGTTCAACAACTCGTACGCCTGCCAGAACTCGAAG
 P  F  A  D  A  V  R  A  G  V  G  S  S  V  M  C  S  Y  Q  Q  F  N  N  S  Y  A  C  Q  N  S  K
12345678901234567890123456789012345678901234567890123456789012345678901234567890123456789012345678901234567890
    72            73            74            75            76            77            78            79            80        8
CTGCTGAACGACCTCCTCAAGAACGAGCTTGGGTTTCAGGGCTTCGTCATGAGCGACTGGCAGGCACACAGCGCCGGCGCAGCAAGCGCC
 L  L  N  D  L  L  K  N  E  L  G  F  Q  G  F  V  M  S  D  W  Q  A  Q  H  T  G  A  A  S  A
12345678901234567890123456789012345678901234567890123456789012345678901234567890123456789012345678901234567890
   81            82            83            84            85            86            87            88            89       9
GTGGCTGGTCTCGATATGTCCATGCCGGGCGACACCCAGTTCAACACTGGCGTCAGTTTCTGGGGCGCCAATCTCACCCTCGCCGTCCTC
 V  A  G  L  D  M  S  M  P  G  D  T  Q  F  N  T  G  V  S  F  W  G  A  N  L  T  L  A  V  L
12345678901234567890123456789012345678901234567890123456789012345678901234567890123456789012345678901234567890
   90            91            92            93            94            95            96            97            98       9
AACGGCACAGTCCCTGCCTACCGTCTCGACGACATGGCCATGCGCATCATGGCCGCCCTCTTCAAGGTCACCACCGACCTGGAA
 N  G  T  V  P  A  Y  R  L  D  D  M  A  M  R  I  M  A  A  L  F  K  V  T  T  D  L  E
12345678901234567890123456789012345678901234567890123456789012345678901234567890123456789012345678901234567890
   99           100           101           102           103           104           105           106           107       1
CCGATCAACTTCTCCTTCTGGACCGACGACACTTATGGCCCCCATGGCCTACCAGGAGATTAATTCCCACGTT
 P  I  N  F  S  F  W  T  D  D  T  Y  G  P  H  W  A  A  K  Q  G  Y  Q  E  I  N  S  H  V
12345678901234567890123456789012345678901234567890123456789012345678901234567890123456789012345678901234567890
   108           109           110           111           112           113           114           115           116       1
GACGTCCGCGCCGACCACGGCAACCTCATCCGGGAGATTGCCGCCAAGGGTACGGTGCTGCTGAAGAATACCGGCTCTCTACCCCTGAAC
 D  V  R  A  D  H  G  N  L  I  R  E  I  A  A  K  G  T  V  L  L  K  N  T  G  S  L  P  L  N
12345678901234567890123456789012345678901234567890123456789012345678901234567890123456789012345678901234567890
   117           118           119           120           121           122           123           124           125       1
AAGCCAAAGTTCGTGGCCGTCATCGGCGAGGATGCTGGGTCTGAGCCCCAACGGGCCCCAAACGGGCCCAAACGGGCTGTAACGAAGGC
 K  P  K  F  V  A  V  I  G  E  D  A  G  S  S  P  N  G  P  N  G  C  S  D  R  G  C  N  E  G
12345678901234567890123456789012345678901234567890123456789012345678901234567890123456789012345678901234567890
   126           127           128           129           130           131           132           133           134       1
```

```
GCCCCGACGTTTGGCAACTTCTCTCCACCGACCTCGAGGACTATCTCTTCCCCAAGGACGAGTTCCCCTACATCTACCAGTACATCTACCCG
 A  P  T  F  G  N  F  S  T  D  L  E  D  Y  L  F  P  K  D  E  F  P  Y  I  Y  Q  Y  I  Y  P
207      208       209       210       211       212       213       214       215       2
TACCTCAACACGACCGACCCCCGAGGGCCTCGGCCGATCCCCACTACGGCCGAGAGTTCCTCCCGCCCCACGCCACCGAT
 Y  L  N  T  T  D  P  R  R  A  S  A  D  P  H  Y  G  Q  T  A  E  E  F  L  P  P  H  A  T  D
216       217       218       219       220       221       222       223       224       2
GACGACCCCCAGCCGCCTCCTCCGGTCCTCCGGTCCCGGGCGGAAACTCCCCCGGCGCAACCGCTGTACGACATTGTCTACACAATCACGGCC
 D  D  P  Q  P  P  L  L  R  S  S  G  G  N  S  P  G  G  N  R  Q  L  Y  D  I  V  Y  T  I  T  A
225       226       227       228       229       230       231       232       233       2
GACATCACGAATACGGGGCTCCGTTGTAGGCGAGGAGGTACCGCAGCTCTACGTCTCGCTTGGGCGGTCCCGAGGATCCCAAGGTGCAGCTG
 D  I  T  N  T  G  S  V  V  G  E  E  V  P  Q  L  Y  V  S  L  G  G  P  E  D  P  K  V  Q  L
234       235       236       237       238       239       240       241       242       2
CGCGACTTTGACAGGATGCGCATCGAACCCGGCGAGTTCCGCCAGTTCACCGGCCGCCTGACGCGCCGAGATCTGAGCAACTGGGACGTC
 R  D  F  D  R  M  R  I  E  P  G  E  F  R  Q  F  T  G  R  L  T  R  R  D  L  S  N  W  D  V
243       244       245       246       247       248       249       250       251       2
ACGGTGCAGGACTGGGTCATCAGCAGGTATCCCAAGACGGCCATATGTTGGGAGGAGCAGCCGGAAGTTGGATCTCAAGATTGAGCTTCCT
 T  V  Q  D  W  V  I  S  R  Y  P  K  T  A  Y  V  G  R  S  S  R  K  L  D  L  K  I  E  L  P
252       253       254       255       256       257       258       259       260
tga
 *
261
```

FIG. 2D

C1 CBH1a promoter sequence (SEQ ID NO:8)

GAGCTCCACCGCGGTGGCGGCCGCGCGGATCTTACAAAAAAAGGTATCCGATTTGGGGAACGTCGATGAAGTATTGCAAAAGTGACGAGAGTTGCGCAACTA
ACTCGCTGCCGAAGAAGCTGCGGAAGAGAGAACACCGAAAGTGAATAACGTTACGGATGTCCTGACCTCAAAGTTGAAACCAGCCTTCCTGC
TCTATTTGGGAAAGCGGCTTGCCCTTGAATGCGCTGCACTGTGGCACGACTACCAGTGATCGGAGGAGCAAACTACCCTGGTCCGTTCCTTGGTG
GGCGGCACTAGGCCCAACTTAGGGTGATCGGAGGTCGATGCCGGCCAGAGACCGACAATCACCGCGGTCTGCATTCCCAAGTATATTGAAGATGGCACCAGTAC
CACCTGCTGATCGCCCGCCAGTCGTTTGCGTCCGATGAGGTTGCGCCCAAATTGGGAGTTTTTGAAGGCCTCTCTCCCGCACATCAGAAATCAAGATGAAGTC
CCGGTTTTGCGTCCAGTCCGTTTGGTGCCAAATTGGGAGTTTTTGAAGGCCTCTCTCCCGCACATCAGAAATCAGAAGAAATCAAGATGAAGACCG
GCACACACGGCGAGTTCCACGGACTACACTAAAATGCGGGGAGAAGCGAGATCCGTTGCGAAGGGAAGGGATGGGGTTGCTCGTGCGCGTCAGGGCGGA
GGGTAAGTGGGCCCTTTGCTTGAATCTAGTGTACACCGGCACTTCGCGAGAGTAGGCTCCGAAGGAGTACGCGTCAAATACGTCTTCTGCGAGCATCGTGA
CGTGCGCCCTTTGCTTGAATCTAGTGTACACCGGCACTTCGCGAGAGTAGGCTCCGAAGGAGTATCTACGGCGTCAAATACGTCTTCTGCGAGCATCGTGA
GACGAGCAGGCGACAGGAGCCTCGGACGGCGGGCCCTTCGCCCTTGCCCTGCCCGACAATCGTTAATCGCTCCTGCACGATGCCCTCAGT
ACCAAGTTCTTCCGCAGGTGTGGCAACCATAACGTGACATCGCCGCCTTCCATCGCTTCCATCGCCGGTTAGCGCACGACCGCTTGCCCCTTCGTCCTTGAC
CCGTGCCGCCGGTGCAACCATAACGTGACATCGCCGCCTTCCATCGCTTCCATCGCCGGTTAGCGCACGACCGCTTGCCCCTTCGTCCTTGAC
TCGGGCCTCTACTCTGATCGCCATCTTGCCACCGACGCCCGCCCCCTTTTTTTCTCCCTGCCGGCAGGTCGGTGGCCCGCGCCGTCTCCCACGTACGG
TATCTCCCAGACCTCTTGCCATCTTGACGACCATCATTCGTAATGATACCCAACACCGGGCCGTTCCCGAGGGCGCCCGCGAATTAGCCTGGAAGCGGCTGCCCG
AACCTCGTTGTACAGTACCTCTCGTAATGATACCCAACACCGGGCCGTTCCCGAGGGCGCCGACATCCCGAGAAGCCGGAAGCGGCTGCCCG
GCTGACCTTTGTGACTTGGCGATGAGCGGCAGCCCTCGTCTTCAGATCAAGCAACTGTGTGCTGATCCTCTTCCGT

FIG. 4

Polynucleotide sequence encoding C1 β-glucosidase 1 (BGL1) protein using codons biased
for expression in *Saccharomyces cerevisiae* (SEQ ID NO:9)

```
ATAGAAAGTAGAAAGGTA
 I  E  S  R  K  V

CATCAAAAACCATTAGCTAGATCAGAACCCATTCTCTCCATGGATGAACCCTAATGCAGATGGGCAGAAGCATATGCTCAG
 H  Q  K  P  L  A  R  S  E  P  P  F  Y  P  S  P  W  M  N  P  N  A  D  G  W  A  E  A  Y  A  Q

GCCAAGAGTTTTGTCTCCCAGATGACTCTGTTGGAAAAGGTTAATCTGACAACAGGAGTAGGGTGCAGAACAGTGTGTCGGCCAA
 A  K  S  F  V  S  Q  M  T  L  L  E  K  V  N  L  T  T  G  V  G  W  G  A  E  Q  C  V  G  Q

GTTGGTGCTATCCCTAGATTGGGTCTTAGAAGTTTGTGTATGCACGATTCTCCCTTAGGTATAAGAGGCGCTGACTATAACTCAGCATTC
 V  G  A  I  P  R  L  G  L  R  S  L  C  M  H  D  S  P  L  G  I  R  G  A  D  Y  N  S  A  F

CCATCCGGGCAAACTGTTGCTGCGACAGTGGGACATGGGCGGTTTGATGTATAGAAGGGGTTATGCGATGGGTCAAGAGCAAAAGGTAAAGGA
 P  S  G  Q  T  V  A  A  T  W  D  R  G  L  M  Y  R  R  G  Y  A  M  G  Q  E  A  K  G  K  G

ATTAATGTATTGTTGGGCCGGTCCTGTGGCCGGTCCTTTGGGAAGAATGCCAGAAGGTGGAAGAACTGGAAGATTCGCCCCGACCCAGTG
 I  N  V  L  L  G  P  V  A  G  P  L  G  R  M  P  E  G  G  R  N  W  E  G  F  A  P  D  P  V

CTAACAGGTATAGGTATGTCCGAAACGATCAAAGGCATACAAGATGCAGGTGTTATCGCCTGTGCGAAGCATTTTATTGGTAATGAACAA
 L  T  G  I  G  M  S  E  T  I  K  G  I  Q  D  A  G  V  I  A  C  A  K  H  F  I  G  N  E  Q

GAGCATTTCGTCAAGTGCCAGAGGCTCCAAGGTTATGGTTATAATATTTCTGAAACTTTAAGTTCCAACATCGATGACAAAACCATGCAC
 E  H  F  R  Q  V  P  E  A  Q  G  Y  G  Y  N  I  S  E  T  L  S  S  N  I  D  D  K  T  M  H

GAGTTATACTTATGGCCTTTTGCAGATGCGCTGTGAGAGCGCGTTGGCTCTCGTTATGTGCTCTTATCAGCAAGTTAATAACTCTTACGCC
 E  L  Y  L  W  P  F  A  D  A  V  R  A  G  V  G  S  V  M  C  S  Y  Q  Q  V  N  N  S  Y  A

TGTCAAAATTCCAAGTTACTAAATGACTTATTGAAGAACGAACTAGGATTCCAAGGATTCGTCATGAGCGATTGGCAAGCACAGCATACT
 C  Q  N  S  K  L  L  N  D  L  L  K  N  E  L  G  F  Q  G  F  V  M  S  D  W  Q  A  Q  H  T
```

FIG. 5A

```
GGTGCTGCATCCGCTGTGGCAGGATTAGATATGTCAATGCCAGGAGATACACAATTTAATACTGGCGTTAGTTTTTGGGGTGCAAACCTA
 G  A  A  S  A  V  A  G  L  D  M  S  M  P  G  D  T  Q  F  N  T  G  V  S  F  W  G  A  N  L

ACTTTAGCTGTGTTCTAAACGGTACGGTACCTGCATATCGTTTAGACGACATGGCCATGCGTATAATGGCTGCTGTTATTCAAAGTTACAAAA
 T  L  A  V  L  N  G  T  V  P  A  Y  R  L  D  D  D  M  A  M  R  I  M  A  A  L  F  K  V  T  K

ACCACCGATTTAGAACCAATTAATTTAGTTTTTGGACAGATGACACATATGTCCTATACACTGGGCTGCTAAGCAAGGTACCAAGAA
 T  T  D  L  E  P  I  N  F  S  F  W  T  D  D  T  Y  G  P  I  H  W  A  A  K  Q  G  Y  Q  E

ATAAATAGTCACGTTGACGTTAAGAGAGCGGATCAATCTTATCAGAGAGATAGCAGAAACTGTATTGTTGAAGAATACTGGT
 I  N  S  H  V  D  V  R  A  D  H  G  N  L  I  R  E  I  A  A  K  G  T  V  L  L  K  N  T  G

TCATTACCACTAAACAAACCAAAGTTTGTCGCAGTCATTGGTGAAGATGTCTGGTTCATCCCCTAATTGGTCTCTCCGGATGCGGCTTTACAGGCT
 S  L  P  L  N  K  P  K  F  V  A  V  I  G  E  D  A  G  S  S  P  N  G  P  N  G  C  S  D  R

GGCTGCAATGAAGGCACGTTGGCAATGGGCGTTGGGGCTCAGGGACTGCCAATTACCCCTATTGGTCTCTCCGGATGCGGCTTTACAGGCT
 G  C  N  E  G  T  L  A  M  G  W  G  S  G  T  A  N  Y  P  Y  L  V  S  P  D  A  A  L  Q  A

AGAGCAATCCAGGATGGTACTAGATACGAGAGCGTCCTAAGTAACTATGCCGAAGAAAAGACTAAGGCCTTAGTCAGTCAAGCCAATGCC
 R  A  I  Q  D  G  T  R  Y  E  S  V  L  S  N  Y  A  E  E  K  T  K  A  L  V  S  Q  A  N  A

ACTGCTATCGTTTTCGTAAACGCGGATTCTGGCGAAGGTTATATCAATGTTGATGGTAATGAAGGTGACAGAAAGAATTTAACTTTATGG
 T  A  I  V  F  V  N  A  D  S  G  E  G  Y  I  N  V  D  G  N  E  G  D  R  K  N  L  T  L  W

AATAACGGGCGACACATTAGTGTTAAAAATGTATCAGGAATCAGGAGAATCAGGAAATTCCATTACGGACGTACTATAC
 N  N  G  D  T  L  V  K  N  V  S  S  W  C  S  N  T  I  V  V  I  H  S  V  G  P  V  L  L  T

GACTGGTACGATAACCCAAACCAATTACCGCCAGGAGCTCTGCCAGGTCAGGTGCAGGAATCAGGAAATTCCATTACGGACGTACTATAC
 D  W  Y  D  N  P  N  I  T  A  I  L  W  A  G  L  P  G  Q  E  S  G  N  S  I  T  D  V  L  Y

GGAAAGGTTAACCCAGCCGCCAGGAGCTACGGGTAAGACAAGAGAGAGCTACGGAGCTGATGTTCTTTATAAACCGAACAAC
 G  K  V  N  P  A  A  R  S  P  F  T  W  G  K  T  R  E  S  Y  G  A  D  V  L  Y  K  P  N  N
```

FIG. 5B

```
GGGAATGGAGCGCCCACAGCAAGATTTACTGAAGGTGTGTTCATTGACTATAGATACTTCGACAAAGTTGACGATGACTCAGTTATATAT
 G  N  G  A  P  Q  Q  D  F  T  E  G  V  F  I  D  Y  R  Y  F  D  K  V  D  D  D  S  V  I  Y

GAATTCGGTCACGGTCTCTATCTTATACTACTTTTGAATATTCAAAAGTAGTCAAAAGTGTTTCTGAATATAGGCCGACCACC
 E  F  G  H  G  L  S  Y  T  T  F  E  Y  S  N  I  R  V  V  K  S  N  V  S  E  Y  R  P  T  T

GGAACGACGGCTCAAGCGCCTACCTTCGGTAATTTTCAACGGATTTAGAAGATTATTATTTCCCAAAGACGAATTCCATACATCTAC
 G  T  T  A  Q  A  P  T  F  G  N  F  S  T  D  L  E  D  Y  L  F  P  K  D  E  F  P  Y  I  Y

CAATACATATACCCCTATCTGAATACTACCCAAGAAGAGCTTCTGCCGATCCACATTACGGGCAGACTGCCGAAGAGTTCTTGCCA
 Q  Y  I  Y  P  Y  L  N  T  T  D  P  R  R  A  S  A  D  P  H  Y  G  Q  T  A  E  E  F  L  P

CCACACGCTACTGACGACGATCCTCAACCTCTTCTGAGGTCCAGTGGCGGAAATTCACCTGGTGGTAATAGGCAGCTGTATGATATTGTG
 P  H  A  T  D  D  D  P  Q  P  L  L  R  S  S  G  G  N  S  P  G  G  N  R  Q  L  Y  D  I  V

TATACTATAACGGCTGATATTACTAATACTGGTAGCGTTGTTGGTGAAGAAGTGCCGCAATTATATGTGTCTTTAGGTGGTCCGGAAGAT
 Y  T  I  T  A  D  I  T  N  T  G  S  V  V  G  E  E  V  P  Q  L  Y  V  S  L  G  G  P  E  D

CCTAAGGTTCAGTTAAGAGACTTTGATAGGATGAGAATAGAACCTGGAGAGAAATAGGCAATTACAGGTAGATTGACCCGTAGGGATCTG
 P  K  V  Q  L  R  D  F  D  R  M  R  I  E  P  G  E  T  R  Q  F  T  G  R  L  T  R  R  D  L

TCAAACTGGGATGTAACAGTGCAAGATTGGGTAATCAGCAGGTACCCGAAAACTGCATACGTGGTAGATCTTCCCGTAAGTTAGATTTG
 S  N  W  D  V  T  V  Q  D  W  V  I  S  R  Y  P  K  T  A  Y  V  V  G  R  S  R  K  L  D  L

AAAATTGAATTGCCATAA
 K  I  E  L  P  *
```

POLYNUCLEOTIDES ENCODING RECOMBINANT C1 BETA-GLUCOSIDASE FOR PRODUCTION OF SUGARS FROM CELLULOSIC BIOMASS

CROSS-REFERENCE TO RELATED APPLICATIONS

This application claims benefit of U.S. provisional application No. 61/247,379, filed Sep. 30, 2009, the entire content of which is incorporated herein by reference.

FIELD OF THE INVENTION

The invention relates to expression of a recombinant β-glucosidase and its use in the production of fermentable sugars from cellulosic biomass.

BACKGROUND OF THE INVENTION

Cellulosic biomass is a significant renewable resource for the generation of sugars. Fermentation of these sugars can yield commercially valuable end-products, including biofuels and chemicals currently derived from petroleum. While the fermentation of simple sugars to ethanol is relatively straightforward, the efficient conversion of cellulosic biomass to fermentable sugars such as glucose is challenging. See, e.g., Ladisch et al., 1983, *Enzyme Microb. Technol.* 5:82. Cellulosic material may be pretreated chemically, mechanically or in other ways to increase the susceptibility of cellulose to hydrolysis. Such pretreatment may be followed by the enzymatic conversion of cellulose to glucose, cellobiose, cello-oligosaccharides and the like, using enzymes that specialize in breaking down the β-1-4 glycosidic bonds of cellulose. These enzymes are collectively referred to as "cellulases".

Cellulases are divided into three sub-categories of enzymes: 1,4-β-D-glucan glucanohydrolase ("endoglucanase" or "EG"); 1,4-β-D-glucan cellobiohydrolase ("exoglucanase", "cellobiohydrolase", or "CBH"); and β-D-glucoside-glucohydrolase ("β-glucosidase", "cellobiase" or "BG"). Endoglucanases randomly attack the interior parts and mainly the amorphous regions of cellulose, mostly yielding glucose, cellobiose, and cellotriose. Exoglucanases incrementally shorten the glucan molecules by binding to the glucan ends and releasing mainly cellobiose units from the ends of the cellulose polymer. β-glucosidases split the cellobiose, a water-soluble β-1,4-linked dimer of glucose, into two units of glucose. Efficient production of cellulases for use in processing cellulosic biomass would reduce costs and increase the efficiency of production of biofuels and other commercially valuable compounds.

SUMMARY OF THE INVENTION

In one aspect the invention provides a method of producing a secreted β-glucosidase polypeptide, by culturing a cell comprising a polynucleotide sequence encoding C1 β-glucosidase (SEQ ID NO:3) or an enzymatically active variant thereof, operably linked to a heterologous promoter, under conditions in which β-glucosidase is produced. The cell may be a C1 strain cell. Alternatively, the cell may be other than a C1 strain cell. In some cases the heterologous promoter is the C1 cellobiohydrolase (CBH1a) promoter. In some cases the polynucleotide sequence does not encode one or more of SEQ ID NO:11, SEQ ID NO:30, or SEQ ID NO:31. Optionally the polynucleotide sequence encodes SEQ ID NO:4.

In one aspect the invention provides a method for producing glucose from cellobiose, by contacting cellobiose with a recombinant cell comprising a polynucleotide sequence encoding C1 β-glucosidase (SEQ ID NO:3) or an enzymatically active variant thereof, operably linked to a heterologous promoter, under conditions in which β-glucosidase is expressed and secreted by the cell and said cellobiose is enzymatically converted by said β-glucosidase to glucose. The cell may be a C1 strain cell. Alternatively, the cell may be other than a C1 strain cell. In some cases the heterologous promoter is the C1 cellobiohydrolase 1a (CBH1a) promoter. In some cases the polynucleotide sequence does not encode one or more of SEQ ID NO:11, SEQ ID NO:30, or SEQ ID NO:31. Optionally the polynucleotide encodes SEQ ID NO:4.

Also contemplated is a method of converting a biomass substrate to a fermentable sugar, by combining recombinant β-glucosidase made according to the invention, with the biomass substrate (e.g., cellobiose) under conditions suitable for the production of the fermentable sugar. In some cases the method includes the step of recovering the β-glucosidase from the medium in which the cell is cultured. In one aspect a composition comprising the recombinant β-glucosidase is provided.

In one aspect, the invention provides a recombinant host cell comprising a polynucleotide sequence encoding C1 β-glucosidase (SEQ ID NO:3), or a variant thereof, operably linked to a heterologous promoter. Optionally the polynucleotide encodes SEQ ID NO:4. In one embodiment the recombinant host cell expresses at least one other recombinant cellulase enzyme. Also contemplated is a method of converting a biomass substrate to a fermentable sugar, by combining the recombinant cell with the biomass substrate under conditions suitable for the production of the fermentable sugar.

Also provided are is a cell comprising a polynucleotide sequence encoding C1 β-glucosidase (SEQ ID NO:3), or an enzymatically active variant thereof as described herein, wherein the encoding sequence does not comprise an intron, and optionally is operably linked to heterologous promoter, which may be a C1 cellobiohydrolase 1 a (CBH1a) promoter. In one embodiment, the cell expresses at least one additional recombinant cellulase enzyme.

Also provided is a composition containing a cell comprising a polynucleotide sequence encoding C1 β-glucosidase (SEQ ID NO:3) or an enzymatically active variant thereof, as described herein, and a β-glucosidase protein secreted by the cell. In one aspect a recombinant cell described herein is contacted with a biomass substrate (e.g., cellobiose) and the substrate is converted to a fermentable sugar (e.g., glucose).

BRIEF DESCRIPTION OF THE FIGURES

FIGS. 1A-F shows the genomic (SEQ ID NO:1) and cDNA (SEQ ID NO:2) sequences encoding the C1 β-glucosidase 1 (BGL1) protein. The genomic sequence is above and aligned with the lower cDNA sequence. Gaps in the lower sequence show the positions of introns.

FIGS. 2A-D shows the BGL1 cDNA sequence (SEQ ID NO:2) and the corresponding protein sequence. The predicted signal peptide and corresponding nucleotide sequence are in bold font. The amino acid sequence including the signal peptide sequence is SEQ ID NO:4. The amino acid sequence not including the signal peptide sequence is SEQ ID NO:3.

FIG. 4 shows the 5' (promoter) sequence of the C1 cbh1a gene (SEQ ID NO:8).

FIGS. 5A-C shows an artificial polynucleotide sequence encoding a C1 β-glucosidase 1 (BGL1) secreted protein (SEQ ID NO:9). The sequence has a codon usage bias to optimize expression in *Saccharomyces cerevisiae*.

DETAILED DESCRIPTION OF THE INVENTION

I. Definitions

Figure 3:
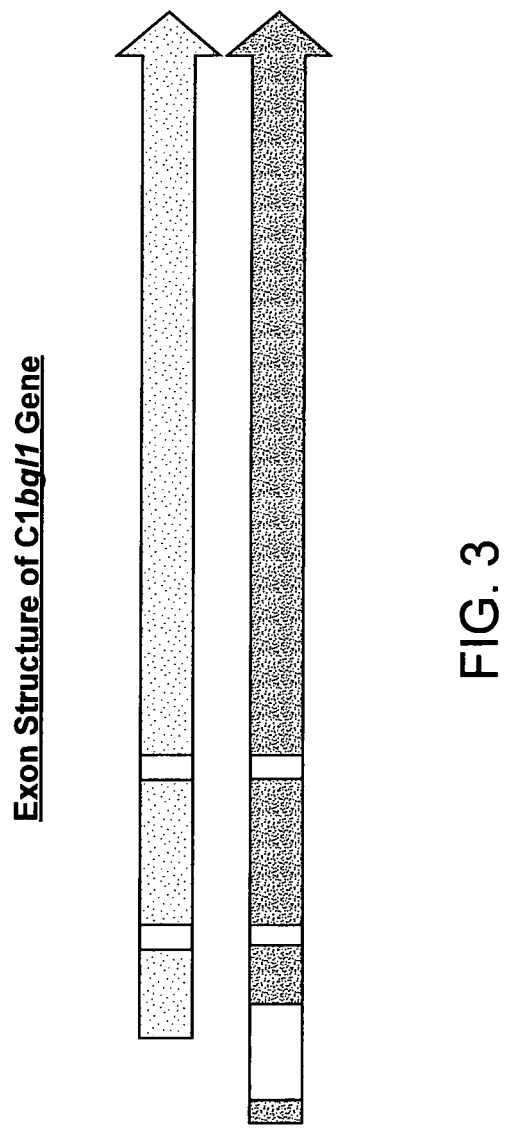
FIG. 3 illustrates the exon structure of the bgl1 gene (lower arrow) compared to a previously described exon structure (upper arrow).

The following definitions are provided to assist the reader. Unless otherwise defined, all terms of art are intended to have the meanings commonly understood by those of skill in the molecular biology and microbiology arts. In some cases, terms with commonly understood meanings are defined herein for clarity and/or for ready reference, and the inclusion of such definitions herein should not necessarily be construed to represent a substantial difference over the definition of the term as generally understood in the art.

The term "cellulase" refers to a category of enzymes capable of hydrolyzing cellulose (β-1,4-glucan or β-D-glucosidic linkages) to shorter oligosaccharides, cellobiose and/or glucose.

The term "β-glucosidase" or "cellobiase" used interchangeably herein means a β-D-glucoside glucohydrolase which catalyzes the hydrolysis of a sugar dimer, including but not limited to cellobiose, with the release of a corresponding sugar monomer. In one embodiment, a β-glucosidase is a β-glucosidase glucohydrolase of the classification E.C. 3.2.1.21 which catalyzes the hydrolysis of cellobiose to glucose. Some of the β-glucosidases have the ability to also hydrolyze β-D-galactosides, β-L-arabinosides and/or β-D-fucosides and further some β-glucosidases can act on α-1,4-substrates such as starch. β-glucosidase activity may be measured by methods well known in the art, including the assays described hereinbelow.

The term "β-glucosidase polypeptide" refers herein to a polypeptide having β-glucosidase activity.

The term "β-glucosidase polynucleotide" refers to a polynucleotide encoding a polypeptide having β-glucosidase activity.

"Cellulolytic activity" encompasses exoglucanase activity (CBH), endoglucanase (EG) activity and/or β-glucosidase activity.

The term "exoglucanase", "exo-cellobiohydrolase" or "CBH" refers to a group of cellulase enzymes classified as E.C. 3.2.1.91. These enzymes hydrolyze cellobiose from the reducing or non-reducing end of cellulose.

The term "endoglucanase" or "EG" refers to a group of cellulase enzymes classified as E.C. 3.2.1.4. These enzymes hydrolyze internal β-1,4 glucosidic bonds of cellulose.

As used herein, the term "isolated" refers to a nucleic acid, polynucleotide, polypeptide, protein, or other component that is partially or completely separated from components with which it is normally associated (other proteins, nucleic acids, cells, synthetic reagents, etc.).

The term "wildtype" as applied to a polypeptide (protein) means a polypeptide (protein) expressed by a naturally occurring microorganism such as bacteria or filamentous fungus. As applied to a microorganism, the term "wildtype" refers to the native, non-recombinant micro-organism.

A nucleic acid (such as a polynucleotide), a polypeptide, or a cell is "recombinant" when it is artificial or engineered, or derived from or contains an artificial or engineered protein or nucleic acid. A recombinant nucleic acid, or equivalently, polynucleotide, is one that is inserted into a heterologous location such that it is not associated with nucleotide sequences that normally flank the nucleic acid as it is found in nature. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. Examples of recombinant nucleic acids include a protein-encoding DNA sequence that is (i) operably linked to a heterologous promoter and/or (ii) encodes a fusion polypeptide with a protein sequence and a heterologous signal peptide sequence. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

Nucleic acids "hybridize" when they associate, typically in solution. Nucleic acids hybridize due to a variety of well-characterized physico-chemical forces, such as hydrogen bonding, solvent exclusion, base stacking and the like. As used herein, the term "stringent hybridization wash conditions" in the context of nucleic acid hybridization experiments, such as Southern and Northern hybridizations, are sequence dependent, and are different under different environmental parameters. An extensive guide to the hybridization of nucleic acids is found in Tijssen (1993) "Laboratory Techniques in biochemistry and Molecular Biology-Hybridization with Nucleic Acid Probes," Part I, Chapter 2 (Elsevier, New York), which is incorporated herein by reference. For polynucleotides of at least 100 nucleotides in length, low to very high stringency conditions are defined as follows: pre-hybridization and hybridization at 42° C. in 5×SSPE, 0.3% SDS, 200 µg/ml sheared and denatured salmon sperm DNA, and either 25% formamide for low stringencies, 35% formamide for medium and medium-high stringencies, or 50% formamide for high and very high stringencies, following standard Southern blotting procedures. For polynucleotides of at least 100 nucleotides in length, the carrier material is finally washed three times each for 15 minutes using 2×SSC, 0.2% SDS at least at 50° C. (low stringency), at least at 55° C. (medium stringency), at least at 60° C. (medium-high stringency), at least at 65° C. (high stringency), and at least at 70° C. (very high stringency).

The term "culturing" or "cultivation" refers to growing a population of microbial cells under suitable conditions in a liquid or solid medium. In some embodiments, culturing refers to fermentative bioconversion of a cellulosic substrate to an end-product.

The term "contacting" refers to the placing of a respective enzyme in sufficiently close proximity to a respective substrate to enable the enzyme to convert the substrate to a product. Those skilled in the art will recognize that mixing solution of the enzyme with the respective substrate will effect contacting.

As used herein the term "transformed" or "transformation" used in reference to a cell means a cell has a non-native nucleic acid sequence integrated into its genome or as an episomal plasmid that is maintained through multiple generations.

The term "introduced" in the context of inserting a nucleic acid sequence into a cell means transfected, transduced or transformed (collectively "transformed") and prokaryotic cell wherein the nucleic acid is incorporated into the genome of the cell.

As used herein, "C1" refers to a fungal strain described by Garg, A., 1966, "An addition to the genus *Chrysosporium corda*" *Mycopathologia* 30: 3-4. "*Chrysosporium lucknowense*" and includes the strains described in U.S. Pat. Nos.

6,015,707, 5,811,381 and 6,573,086; US Pat. Pub. Nos. 2007/0238155, US 2008/0194005, US 2009/0099079; International Pat. Pub. Nos., WO 2008/073914 and WO 98/15633, and any derivatives thereof, and include, without limitation, Chrysosporium lucknowense Garg 27K, VKM-F 3500 D (Accession No. VKM F-3500-D), C1 strain UV13-6 (Accession No. VKM F-3632 D), C1 strain NG7C-19 (Accession No. VKM F-3633 D), and C1 strain UV18-25 (VKM F-3631 D), all of which have been deposited at the All-Russian Collection of Microorganisms of Russian Academy of Sciences (VKM), Bakhurhina St. 8, Moscow, Russia, 113184, and any derivatives thereof. Although initially described as *Chrysosporium lucknowense*, C1 may currently be considered a strain of *Myceliophthora thermophila*. Other C1 strains include cells deposited under accession numbers ATCC 44006, CBS (Centraalbureau voor Schimmelcultures) 122188, CBS 251.72, CBS 143.77, CBS 272.77, and VKM F-3500D. Exemplary C1 strains include modified organisms in which one or more endogenous genes or sequences has been deleted and/or one or more heterologous genes or sequences has been introduced. Derivatives include UV18#100fΔalp1, UV18#100f Δpyr5 Δalp1, UV18#100.f Δalp1 Δpep4 Δalp2, UV18#100.f Δpyr5 Δalp1 Δpep4 Δalp2 and UV18#100.f Δpyr4 Δlyr5 Δalp 1 Δpep4 Δalp2. as described in W02008073914, incorporated herein by reference.

When two elements, e.g., a promoter and a coding sequence, are said to be "operably linked," it is meant that the juxtaposition of the two allows them to be functionally active. Thus, a promoter or other control sequence is "operably linked" to a coding sequence when the promoter or control sequence is placed at a position relative to the coding sequence of the DNA sequence so that it controls the transcription of the coding sequence.

As used herein, the terms "identical" or percent "identity," in the context of describing two or more polynucleotide or polypeptide sequences, refer to two or more sequences that are the same or have a specified percentage of nucleotides or residues that are the same when compared and aligned for maximum correspondence over a comparison window or designated region (e.g., the entire length of the reference sequence), as measured by manual alignment and visual inspection or using one of the following sequence comparison algorithms. Methods of alignment of sequences for comparison are well-known in the art. In one embodiment two sequences are aligned (e.g., manually) for optimal identity without introducing gaps in either sequence, or with no more than 1, 2 or 3 gaps of typically less than 10 residues each.

A "comparison window" as used herein, includes reference to a segment of any one of the number of contiguous positions selected from the group consisting of from 20 to 500, usually about 50 to about 300, also about 50 to 250, and also about 100 to about 200 in which a sequence may be compared to a reference sequence of the same number of contiguous positions after the two sequences are optimally aligned. As noted, in some embodiments the comparison is between the entire length of the two sequences, or, if one sequence is a fragment of the other, the entire length of the shorter of the two sequences.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. Examples of algorithms that are suitable for determining percent sequence identity and sequence similarity are the BLAST and BLAST 2.0 algorithms, which are described in Altschul et al., (1990) *J. Mol. Biol.* 215: 403-410 and Altschul et al. (1977) *Nucleic Acids Res.* 25: 3389-3402, respectively. Software for performing BLAST analyses is publicly available at the National Center for Biotechnology Information website, ncbi.nlm.nih.gov. The BLAST algorithm also performs a statistical analysis of the similarity between two sequences (see, e.g., Karlin & Altschul, *Proc. Natl. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

When used herein, the term "coding sequence" is intended to cover a nucleotide sequence, which directly specifies the amino acid sequence of its protein product. The boundaries of the coding sequence are generally determined by an open reading frame, which usually begins with the ATG start codon. The coding sequence typically includes a DNA, cDNA, and/or recombinant nucleotide sequence.

A promoter or other control sequence is "heterologous", when it is operably linked to a sequence encoding a protein sequence with which the promoter is not associated in nature. For example, in a recombinant construct in which the C1 Cbh1a promoter is operably linked to a protein coding sequence other than the C1 Cbh1 a protein coding sequence, the promoter is heterologous. For example, in a construct comprising a C1 Cbh1a promoter operably linked to a C1 β-glucosidase 1 encoding sequence, the promoter is heterologous.

As used herein, the term "expression" includes any step involved in the production of the polypeptide including, but not limited to, transcription, post-transcriptional modification, translation, post-translational modification, and secretion.

The term "expression vector" refers herein to a DNA molecule, linear or circular, that comprises a segment encoding a polypeptide of the invention, and which is operably linked to additional segments that provide for its transcription.

A polypeptide is "enzymatically active" when it has β-glucosidase activity.

The term "pre-protein" refers to a secreted protein with an amino-terminal signal peptide region attached. The signal peptide is cleaved from the pre-protein by a signal peptidase prior to secretion to result in the "mature" or "secreted" protein.

As used herein, a "start codon" is the ATG codon that encodes the first amino acid residue (methionine) of a protein.

II. Introduction

The fungus C1 produces a variety of enzymes that act in concert to catalyze decrystallization and hydrolysis of cellulose to yield soluble sugars. The C1 genome has been at least partially sequenced, as indicated in U.S. patent publications US 2007/0238155, US 2008/0194005, and US 2009/0099079, incorporated herein by reference for all purposes. FIG. 13 of patent publication US 2007/0238155 provides sequence information for the C1 β-glucosidase 1 (bgl1) gene and the encoded protein (BGL1). As discussed in Examples 1 and 2, below, it has now been discovered that this previously published bgl1 gene sequence included sequencing errors. Moreover, surprisingly, the exon structure of the published bgl1 sequence is incorrect. As a consequence of these errors, the available C1 BGL1 protein sequence includes errors, particularly in the signal peptide and at the amino terminus of the mature (i.e., secreted) BGL1 protein.

As discussed in greater detail below, the correct sequence of the BGL1 pre-protein is set forth herein as SEQ ID NO:3 and the correct sequence of the BGL1 secreted protein is set forth as SEQ ID NO:4. Table 1 provides a summary of sequences frequently referred to in this disclosure.

TABLE 1

| SEQ ID NO.: | Description | |
|---|---|---|
| 1 | C1 bgl gene sequence | nucleotide |
| 2 | C1 cDNA sequence | nucleotide |
| 3 | BGL secreted protein | amino acid |
| 4 | BGL pre-protein | amino acid |
| 5 | BGL secreted protein amino terminus (IESRK) | amino acid |
| 6 | BGL signal peptide (MKAAALSCLFGSTLAVAGA) | amino acid |
| 7 | BGL preprotein amino terminus (MKAAALSCLFGSTLAVA-GAIESRK) | amino acid |
| 8 | C1 Cbh1a promoter sequence | nucleotide |
| 9 | Artificial polynucleotide encoding C1 BGL1 protein (codon optimized for expression in S cerevisiae) | nucleotide |
| 13-17 | Flanking sequence 5' to BGL1 start codon | nucleotide |
| 18 | bgl1 intronic sequence | nucleotide |
| 19 | bgl1 intronic sequence fragment | nucleotide |
| 20 | Exon 1 sequence of bgl1 | nucleotide |
| 21 | Exon 1 and Intron 1 of bgl1 | nucleotide |

The C1 β-glucosidase pre-protein and secreted protein, and polynucleotides encoding them, may be used in a variety of applications in which β-glucosidase activity is desired, such as those described hereinbelow. For simplicity, and as will be apparent from context, references to the "C1 BGL1 protein" and the like may be used to refer both to the mature (secreted) form of the protein and to the pre-protein.

In one embodiment, a sequence encoding a C1 BGL1 protein described herein is operably linked to a promoter not associated with BGL1 in nature (i.e., a heterologous promoter), to, for example, improve expression efficiency of the BGL1 protein when expressed in a host cell. In one embodiment the host cell is a fungus, such as a filamentous fungus. In one embodiment the host cell is a C1 strain cell. In one embodiment the host cell C1 and the promoter is the C1 Cbh1a promoter. Advantageously, cultured C1 cells transfected with a vector comprising a C1 β-glucosidase-encoding sequence operably linked to a Cbh1a promoter produced about 35-fold greater β-glucosidase activity than did control cells expressing endogenous bgl1.

The C1 β-glucosidase expression system described herein is particularly useful for production of fermentable sugars from cellulosic biomass. In one aspect the invention relates to a method of producing glucose by contacting a composition comprising cellobiose with a recombinantly expressed C1 β-glucosidase under conditions in which the cellobiose is enzymatically converted to glucose. Purified or partially purified recombinant β-glucosidase protein may be contacted with the cellobiose. Alternatively, recombinant host cells expressing β-glucosidase may be contacted with cellobiose. In one aspect of the present invention, said "contacting" comprises culturing a recombinant host cell in a medium that contains cellobiose produced from a cellulosic feedstock, where the recombinant cell comprises a sequence encoding C1 β-glucosidase operably linked to a heterologous promoter.

In another aspect of the invention, the C1 β-glucosidase signal peptide (SEQ ID NO:6) may be fused to the amino terminus of a polypeptide other than a C1 β-glucosidase (i.e., a "heterologous" polypeptide) to improve secretion, stability, or other properties of the polypeptide when expressed in a host cell, e.g., a fungal cell such as a C1 cell.

Various aspects of the invention are described in the following sections.

III. Properties of B-Glucosidase Proteins For Use In Methods of the Invention

In one aspect the invention provides a method for expressing a β-glucosidase protein by culturing a host cell comprising a vector comprising a nucleic acid sequence encoding wild-type C1 BGL1 (SEQ ID NO:3) operably linked to a heterologous promoter, under conditions in which the β-glucosidase protein, a variant thereof, or an enzymatically active fragment thereof is expressed. Generally the expressed protein comprises a signal peptide, which may be SEQ ID NO:6 (the C1 BGL1 signal peptide) or may be a different signal peptide. In one embodiment, the protein does not comprise one or more of the sequences MQLPAAAQWLLTPAKASL (SEQ ID NO:11), ADNHR (SEQ ID NO:30) or MQL-PAAAQWLLTPAKASLADNHR (SEQ ID NO:31).

In some embodiments the BGL1 polypeptide includes additional sequences which do not alter the encoded activity of a β-glucosidase. For example, the β-glucosidase may be linked to an epitope tag or to other sequence useful in β-glucosidase purification.

In some embodiments the BGL1 protein is a variant that differs from SEQ ID NO:3 at one or more positions. For example, in some embodiments the nucleic acid sequence encodes an enzymatically active BGL1 variant that differs from SEQ ID NO:3 or 4 at one or more positions and which:

a) is substantially identical to SEQ ID NO:3 (secreted protein) and/or is substantially identical to SEQ ID NO:4 (pre-protein);

and b) comprises an amino-terminal sequence set forth as IESRK (SEQ ID NO:5), ESRK (SEQ ID NO:29) or SRK; and/or encodes a pre-protein with an amino-terminal sequence comprising SEQ ID NO:6 or NO:7; and/or comprises at least one, at least two, or three of the following amino acid residues: aspartic acid at position 358 (358ASP), glutamine at position 381 (381GLN), and glutamic acid at position 385 (385GLU) where position numbers correspond to SEQ ID NO:4.

In one embodiment the BGL1 variant protein has substantial sequence identity to SEQ ID NO:3 or SEQ ID NO:4. For example, the BGL1 variant may have an amino acid sequence that is at least about 80% identical, at least about 81% identical, at least about 82% identical, at least about 83% identical, at least about 84% identical, at least about 85% identical, at least about 86% identical, sequence that is at least about 87% identical, at least about 88% identical, at least about 89% identical, at least about 90% identical, at least about 91% identical, at least about 92% identical, at least about 93% identicalsequence that is at least about 94% identical, at least about 95% identical, at least about 96% identical, at least about 97% identical, at least about 98% identical, or at least about 99% identical to SEQ ID NO:3 or SEQ ID NO:4.

Exemplary BGL1 variants may have other insertions, deletions and/or substitutions (including one or more conservative substitutions), as described hereinbelow, whilst remaining substantially identical to the wild-type protein. Mutagenesis and directed evolution methods can be applied to polynucleotides encoding a C1 BGL1 protein to obtain an enzymatically active variants with desirable properties.

Suitable mutagenesis and directed evolution methods are well known in the art. For example, in vitro recombination techniques such as DNA shuffling, staggered extension process (StEP), random chimeragenesis on transient templates (RACHITT), iterative truncation for the creation of hybrid enzymes (ITCHY), recombined extension on truncated templates (RETT), and others have been used to produce proteins with desired properties. In general, polypeptides are expressed from mutagenized polynucleotide sequences and assayed for beta-galatosidase activity (see below) and/or other desirable properties Libraries of these β-glucosidase polypeptide variants may be generated and screened using the high throughput screen for presence of β-glucosidase activity. For example, a polynucleotide encoding a reference β-glucosidase (e.g., SEQ ID NO:3 or SEQ ID NO:4) is subjected to mutagenic processes (for example random mutagenesis and recombination) to introduce mutations into the polynucleotide. The mutated polynucleotide is expressed and translated, thereby generating engineered β-glucosidase enzymes with modifications to the polypeptide. As used herein, "modifications" include amino acid substitutions, deletions, and insertions including for example, those described hereinbelow. Any one or a combination of modifications can be introduced into the naturally occurring enzymatically active polypeptide to generate engineered enzymes, which are then screened by various methods to identify polypeptides having a desired improvement in a specific enzyme property (e.g., enhanced enzymatic activity).

One or more polynucleotides encoding an engineered β-glucosidase with an improved property can be subjected to additional rounds of mutagenesis treatments to generate polypeptides with further improvements in the desired enzyme property and/or other properties. β-glucosidase activity can be determined using any β-glucosidase assay known in the art, such as the para-nitrophenyl-β-D-glucopyranoside (pNPG) and cellobiose assays described below.

In some embodiments the β-glucosidase polypeptide may have a substitution, deletion, and/or insertion, relative to SEQ ID NO: 3. A variety of modifications can be made while preserving (or enhancing) enzymatic activity. Typically the β-glucosidase polypeptide is substantially identical to SEQ ID NO:3 or SEQ ID NO:4.

In some embodiments the BGL1 variant protein differs from SEQ ID NO:3 or SEQ ID NO:4 by having an insertion or one or more amino acids. Such insertions can be at the amino-terminus, the carboxy-terminus or in a non-terminal portion of the protein. In some embodiments, a deletion of from 1 to 2, or from 1 or 2 to 3, 4, 5, 6, 7, 8, 9, 10, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acid residues may be inserted (at the N-terminus, C-terminus and/or nonterminal region of the protein).

In one embodiment the BGL1 protein comprises conservative amino acid substitutions (relative to SEQ ID NO:3 or SEQ ID NO:4) at one or more positions. The concept of conservative substitution is well known and is described herein. The present invention includes conservatively modified variants of the β-glucosidases described herein. These variants have conservative substitutions made in their amino acid sequences. Examples of conservative substitutions are within the group of basic amino acids (arginine, lysine and histidine), acidic amino acids (glutamic acid and aspartic acid), polar amino acids (glutamine and asparagines), hydrophobic amino acids (leucine, isoleucine and valine), aromatic amino acids (phenylalanine, tryptophan and tyrosine), and small amino acids (glycine, alanine, serine, threonine, proline, cysteine and methionine). Amino acid substitutions that do not generally alter the specific activity are known in the art and are described, for example, by H. Neurath and R. L. Hill, 1979, in "The Proteins," Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In some embodiments the β-glucosidase polypeptide variants of the present invention include substitutions of a small percentage, typically less than 5%, more typically less than 2%, and often less than 1% of the amino acids of the polypeptide sequence, e.g., with a conservatively selected amino acid of the same conservative substitution group.

In some embodiments the BGL1 variant includes additional sequences. The addition of sequences which do not alter the encoded activity of a β-glucosidase, such as the addition of a non-functional or non-coding sequence, is considered a conservative variation of the β-glucosidase polypeptide/polynucleotide. For example, the β-glucosidase may be linked to an epitope tag or to other sequence useful in β-glucosidase purification.

Signal Peptide

In general, the β-glucosidase polypeptides are secreted from the host cell in which they are expressed (e.g., C1) and are expressed as a pre-protein including a signal peptide, i.e., an amino acid sequence linked to the amino terminus of a polypeptide and which directs the encoded polypeptide into the cell secretory pathway. In one embodiment, the signal peptide is the endogenous C1 β-glucosidase signal peptide having the sequence set forth as SEQ ID NO:6. In other embodiments, signal peptides from other C1 secreted proteins are used.

Other signal peptides may be used, depending on the host cell and other factors. Effective signal peptide coding regions for filamentous fungal host cells include but are not limited to the signal peptide coding regions obtained from *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola lanuginosa* lipase, and *T. reesei* cellobiohydrolase II. For example, a C1 BGL1 sequence may be used with a variety of filamentous fungal signal peptides known in the art. Useful signal peptides for yeast host cells also include those from the genes for *Saccharomyces cerevisiae* alpha-factor and *Saccharomyces cerevisiae* invertase. Still other useful signal peptide coding regions are described by Romanos et al., 1992, *Yeast* 8:423-488. Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* β-lactamase, *Bacillus stearothermophilus* neutral proteases (nprT, nprS, nprM), and *Bacillus subtilis* prsA. Further signal peptides are described by Simonen and Palva, 1993, *Microbiol Rev* 57: 109-137. Variants of these signal peptides and other signal peptides are suitable.

β-Glucosidase Activity

β-glucosidase proteins used in the method of the invention are enzymatically active or are precursors of enzymatically active protein. β-glucosidase activity can be determined by methods known in the art. In one embodiment β-glucosidase activity is determined using a para-nitrophenyl-β-D-glucopyranoside (pNPG) assay. In one embodiment β-glucosidase activity is determined using a cellobiose assay. Typically an enzymatically active β-glucosidase polypeptide has at least 50% of the enzymatic activity of SEQ ID NO:3.

For example, a colorimetric pNPG (p-nitrophenyl-β-D-glucopyranoside)-based assay may be used to measure β-glucosidase activity. One such assay is described in Example 5, infra. In another exemplary pNPG assay, in a total volume of 100 μL, 20 μL clear media supernatant containing β-glucosidase enzyme is added to 4 mM pNPG (Sigma-Aldrich, Inc. St. Louis, Mo.) solution in 50 mM sodium phosphate buffer at pH 6.5. The reactions are incubated at pH 6.5, 45° C. for 1 hour. The reaction mixture is quenched with 100 μL of 1M sodium carbonate pH 11 solution. The absorbance of the solution is measured at 405 nm to determine the conversion of pNPG to p-nitrophenol. The release of p-nitrophenol ($\epsilon$=17,700 M-1 cm-1) is measured at 405 nm to calculate β-glucosidase activity. Detectable β-glucosidase activity is observed under high throughput screening conditions (pH 7, 50° C.). See Breves et al. (1997) *Appl. Environmental Microbiol.* 63:3902, incorporated hereby reference.

Alternatively β-glucosidase activity may be determined using a cellobiose assay, which used cellobiose as substrate. In a total volume of 100 μL, 25 μL clear media supernatant containing β-glucosidase enzyme is added to 10 g/L cellobiose (Fluka Cat. No. 22150, Sigma-Aldrich, Inc., St. Louis, Mo.) in 100 mM sodium phosphate buffer (pH 6-7) or sodium acetate buffer (pH 5-5.5). The reaction is incubated at 45-70° C. for an appropriate time (25 minutes to overnight depending on the enzyme concentration) while shaking. Glucose production is determined using an enzymatic glucose assay (K-GLUC, Megazyme, Ireland). 10 μl of each reaction is added to 190 μl GOPOD reagent (supplied as part of the K-GLUC assay kit). The reaction is incubated at 45° C. for 20 minutes and the absorbance of the solution was measured at 510 nm. The GOPOD reagent contains 50 mM Potassium phosphate buffer pH 7.4, 0.011M p-hydroxybenzoic acid, 0.008% w/v sodium azide, glucose oxidase (>12,000U/L), peroxidase (>650 U/L) and 80 mg/L 4-aminoantipyrine. The glucose oxidase enzyme in the reagent reacts with any glucose present in the sample and produces hydrogen peroxide which then reacts with the 4-aminoantipyrine to produce a quinoneimine dye in quantities proportionate with the amount of glucose present and can be measured spectrophotometrically at 510 nm.

IV. β-Glucosidase Polynucleotides And Expression Systems

The present invention provides polynucleotide sequences that encode the C1 β-glucosidase (i.e., SEQ ID NOS:3 and 4) as well as the C1 β-glucosidase signal peptide (SEQ ID NO:6). The C1 genomic and cDNA sequences encoding β-glucosidase are set forth as SEQ ID NO:1 and SEQ ID NO:2, respectively. The cDNA sequence encoding the C1 β-glucosidase signal peptide is the sequence from nucleotide 1 to 57 of SEQ ID NO:2. Those having ordinary skill in the art will readily appreciate that due to the degeneracy of the genetic code, a multitude of nucleotide sequences encoding β-glucosidase polypeptides of the present invention exist. Table 2 provides the standard triplet genetic code for each amino acid. For example, the codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide. It is understood that U in an RNA sequence corresponds to T in a DNA sequence. The invention contemplates and provides each and every possible variation of nucleic acid sequence encoding a polypeptide of the invention that could be made by selecting combinations based on possible codon choices.

A DNA sequence may also be designed for high codon usage bias codons (codons that are used at higher frequency in the protein coding regions than other codons that code for the same amino acid). The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. In particular, a DNA sequence can be optimized for expression in a particular host organism. References providing preference information for a wide range of organisms are readily available See e.g., Henaut and Danchin in "*Escherichia Salmonella,*" Neidhardt, et al. Eds., ASM Pres, Washington D.C. (1996), pp. 2047-2066, which is incorporated herein by reference. For illustration, and not for limitation, FIGS. 5A-C shows a C1 BGL1-encoding polynucleotide sequence designed with codon biasing for expression in *Saccharomyces cerevisiae*.

TABLE 2

| GENETIC CODE | | | | | | |
|---|---|---|---|---|---|---|
| Amino acid | | | Codon | | | |
| Alanine | Ala | A | GCA | GCC | GCG | GCU |
| Cysteine | Cys | C | UGC | UGU | | |

TABLE 2-continued

GENETIC CODE

| Amino acid | | | Codon | | | | | |
|---|---|---|---|---|---|---|---|---|
| Aspartic acid | Asp | D | GAC | GAU | | | | |
| Glutamic acid | Glu | E | GAA | GAG | | | | |
| Phenyl-alanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

A variety of methods are known for determining the codon frequency (e.g., codon usage, relative synonymous codon usage) and codon preference in specific organisms, including multivariate analysis, for example, using cluster analysis or correspondence analysis, and the effective number of codons used in a gene (see GCG CodonPreference, Genetics Computer Group Wisconsin Package; Codon W, John Peden, University of Nottingham; McInerney, J. O, 1998, *Bioinformatics* 14:372-73; Stenico et al., 1994, *Nucleic Acids Res.* 222437-46; Wright, F., 1990, *Gene* 87:23-29; Wada et al., 1992, *Nucleic Acids Res.* 20:2111-2118; Nakamura et al., 2000, *Nucl. Acids Res.* 28:292; Henaut and Danchin, "*Escherichia coli* and *Salmonella*," 1996, Neidhardt, et al. Eds., ASM Press, Washington D.C., p. 2047-2066, all of which are incorporated herein be reference). The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (ESTs), or predicted coding regions of genomic sequences (see for example, Mount, D., Bioinformatics: Sequence and Genome Analysis, Chapter 8, Cold Spring Harbor Laboratory Press, Cold Spring Harbor, N.Y., 2001; Uberbacher, E. C., 1996, *Methods Enzymol.* 266: 259-281; Tiwari et al., 1997, *Comput. Appl. Biosci.* 13:263-270, all of which are incorporated herein by reference).

Expression Vectors

The present invention makes use of recombinant constructs comprising a sequence encoding a β-glucosidase as described above. In a particular aspect the present invention provides an expression vector comprising a β-glucosidase polynucleotide operably linked to a heterologous promoter. Expression vectors of the present invention may be used to transform an appropriate host cell to permit the host to express β-glucosidase protein. Methods for recombinant expression of proteins in fungi and other organisms are well known in the art, and number expression vectors are available or can be constructed using routine methods. See, e.g., Tkacz and Lange, 2004, ADVANCES IN FUNGAL BIOTECHNOLOGY FOR INDUSTRY, AGRICULTURE, AND MEDICINE, KLUWER ACADEMIC/ PLENUM PUBLISHERS. New York; Zhu et al., 2009, Construction of two Gateway vectors for gene expression in fungi *Plasmid* 6:128-33; Kavanagh, K. 2005, FUNGI: BIOLOGY AND APPLICATIONS Wiley, all of which are incorporated herein by reference.

Nucleic acid constructs of the present invention comprise a vector, such as, a plasmid, a cosmid, a phage, a virus, a bacterial artificial chromosome (BAC), a yeast artificial chromosome (YAC), and the like, into which a nucleic acid sequence of the invention has been inserted. Polynucleotides of the present invention can be incorporated into any one of a variety of expression vectors suitable for expressing a polypeptide. Suitable vectors include chromosomal, non-chromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated virus, retroviruses and many others. Any vector that transduces genetic material into a cell, and, if replication is desired, which is replicable and viable in the relevant host can be used.

In a preferred aspect of this embodiment, the construct further comprises regulatory sequences, including, for example, a promoter, operably linked to the protein encoding sequence. Large numbers of suitable vectors and promoters are known to those of skill in the art.

Promoter/Gene Constructs

As discussed above, to obtain high levels of expression in a particular host it is often useful to express C1 β-glucosidase under control of a heterologous promoter (such as the C1 cbh1a gene promoter). Typically a promoter sequence may be operably linked to the 5' region of the C1 β-glucosidase coding sequence. It will be recognized that in making such a construct it is not necessary to define the bounds of a minimal promoter. Instead, the DNA sequence 5' to the C1 β-glucosidase start codon can be replaced with DNA sequence that is 5' to the start codon of a given heterologous gene (e.g., cbh1a). This 5' "heterologous" sequence thus includes, in addition to the promoter elements per se, a transcription start signal and the sequence of the 5' untranslated portion of the transcribed chimeric mRNA. Thus, the promoter-gene construct and resulting mRNA will comprise a sequence encoding β-glucosidase and a heterologous 5' sequence upstream to the start codon of the sequence encoding β-glucosidase. In some, but not all, cases the heterologous 5' sequence will immediately abut the start codon of the sequence encoding β-glucosidase.

SEQ ID NOs:13 and 15 represent gene sequence immediately 5' to the start codon of the naturally occurring C1 BGL1 pre-protein, and SEQ ID NOs:14, 16 and 17 are fragments of SEQ ID NO:13 terminating slighty upstream of the start codon. In one embodiment, the recombinant C1 β-glucosidase is expressed from a recombinant gene as a pre-protein that includes the naturally occurring BGL1 signal peptide, and the recombinant gene sequence 5' to the β-glucosidase start codon is not SEQ ID NO:13. More generally, SEQ ID NO:14 is not found within the 100 bases 5' to the β-glucosidase start codon in the recombinant sequence. That is, the recombinant β-glucosidase gene encodes an RNA comprising a sequence encoding SEQ ID NO:4 or a variant thereof, but does not comprise a 5' untranslated sequence containing SEQ ID NO:13, or alternatively does not comprise SEQ ID NO:14 or does not comprise SEQ ID NO:15. In other embodiments the 5' untranslated sequence does not contain SEQ ID NO:15, or alternatively SEQ ID NO:16, or alternatively SEQ ID NO:17.

In one embodiment of the gene construct of the present invention, the C1 β-glucosidase is expressed from the construct as a pre-protein with a heterologous signal peptide, where, in the construct, SEQ ID NO:13 is not 5' to the start codon of the heterologous signal peptide. More generally, in the construct, SEQ ID NO:14 is not found within the 100 bases 5' to the start codon of the heterologous signal peptide. That is, the recombinant β-glucosidase gene construct encodes an RNA comprising a sequence encoding SEQ ID NO:3, or a variant thereof and a heterologous signal peptide, but does not comprise a 5' untranslated sequence containing SEQ ID NO:13. In other embodiments the 5' untranslated sequence does not contain SEQ ID NO:14, or alternatively does not contain SEQ ID NO:15, or alternatively does not contain SEQ ID NO:16, or alternatively does not contain SEQ ID NO:17.

In some embodiments the heterologous promoter is operably linked to a C1 β-glucosidase genomic sequence comprising SEQ ID NO:18, which is the sequence of intron 1 of bgl1.

In some embodiments the heterologous promoter is operably linked to a C1 β-glucosidase cDNA sequence and does not comprise SEQ ID NO:19 (intronic sequence) and/or does not comprise an amino acid sequence encoded in SEQ ID NO:19.

In some embodiments the construct includes SEQ ID NO:20 (the first exon of C1 β-glucosidase) and/or the amino acid sequence encoded in SEQ ID NO:20.

In some embodiments the construct includes SEQ ID NO:21.

Examples of useful promoters for expression of β-glucosidase polynucleotides include promoters from fungi. For example, promoter sequences that drive expression of genes other than the β-glucosidase 1 gene in C1 may be used. For example, a fungal promoter from a gene encoding cellobiohydrolase may be used. In one embodiment the promoter associated with the C1 cellobiohydrolase 1 (cbh1a) gene is used. A promoter sequence associated with cbh1a is provided in FIG. 4. Also see PCT publication WO 01/79507 and U.S. patent publication US 2003/0187243 (both of which are incorporated herein by reference), providing the DNA sequence of the complete C1 CBH1a gene, including promoter and terminator sequences It will be appreciated that a subsequence of SEQ ID NO:8 or a variant of the CBH1a promoter may be used to drive expression of β-glucosidase. In certain embodiments the heterologous promoter operably linked to the β-glucosidase-encoding sequence comprises SEQ ID NO:8, a subsequence of SEQ ID NO:8 with promoter activity or a DNA sequence capable of hybridizing with the complement of SEQ ID NO:8 and having promoter activity. A subsequence of SEQ ID NO:8 having promoter activity can be identified using well known methods. In one approach, a putative promoter sequence is linked 5' to a sequence encoding a reporter protein, the construct is transfected into the host cell (e.g., C1) and the level of expression of the reporter is measured. Expression of the reporter can be determined by measuring, for example, mRNA levels of the reporter sequence, an enzymatic activity of the reporter protein, or the amount of reporter protein produced. For example, promoter activity may be determined by using the green fluorescent protein as coding sequence (Henriksen et al, 1999, *Microbiology* 145: 729-34) or a IacZ reporter gene (Punt et al, 1997, *Gene,* 197:189-93). Functional promoters may be derived from naturally occurring promoter sequences by directed evolution methods. See, e.g. Wright et al., 2005, *Human Gene Therapy,* 16:881-892. In some embodiments the promoter DNA comprises nucleotides 1 to 1817 of SEQ ID NO:8, nucleotides 100 to 1800 of SEQ ID NO:8, nucleotides 200 to 1800 of SEQ ID NO:6, nucleotides 300 to 1800 of SEQ ID NO:8, nucleotides 400 to 1800 of SEQ ID NO:8, nucleotides 500 to 1800 of SEQ ID NO:8, nucleotides 600 to 1800 of SEQ ID NO:8., nucleotides 700 to 1800 of SEQ ID NO:8, nucleotides 800 to 1800 of SEQ ID NO:8, nucleotides 900 to 1800 of SEQ ID NO:8; nucleotides 1000 to 1800 of SEQ ID NO:8, nucleotides 1100 to 1800 of SEQ ID NO:8, nucleotides 1200 to 1800 of SEQ ID NO:8, nucleotides 1300 to 1800 of SEQ ID NO:8, nucleotides 1400 to 1800 of SEQ ID NO:8, nucleotides 1500 to 1800 of SEQ ID NO:8, nucleotides 1600 to 1800 of SEQ ID NO:8, nucleotides 1700 to 1800 of SEQ ID NO:8, or is a polynucleotide that hybridizes under low stringency to the complement of the sequence or subsequence identified above, preferably hybridizes under medium stringency and most preferably hybridizes under high stringency.

Examples of other suitable promoters useful for directing the transcription of the nucleotide constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787, which is incorporated herein by reference), as well as the NA2-tpi promoter (a hybrid of the promoters from the genes for *Aspergillus niger* neutral alpha-amylase and *Aspergillus oryzae* triose phosphate isomerase), promoters such as cbh1, cbh2, egl1, egl2, pepA, hfb1, hfb2, xyn1, amy, and glaA (Nunberg et al., Mol. Cell Biol., 4:2306 -2315 (1984), Boel at al., *EMBO J.* 3:1581-1585 ((1984) and EPA 137280, all of which are incorporated herein by reference), and mutant, truncated, and hybrid promoters thereof. In a yeast host, useful promoters can be from the genes for Saccharomyces cerevisiae enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8:423-488. Promoters associated with chitinase production in fungi may be used. See, e.g., Blaiseau and Lafay, 1992, Gene 120243-248 (filamentous fungus Aphanocladium album); Limon et al., 1995, *Curr. Genet,* 28:478-83 [*Trichoderma harzianum*], both of which are incorporated herein by reference.

Promoters known to control expression of genes in prokaryotic or eukaryotic cells or their viruses and which can be used in some embodiments of the invention include SV40 promoter, *E. coli* lac or trp promoter, phage lambda $P_L$ promoter, tac promoter, T7 promoter, and the like. In bacterial host cells, suitable promoters include the promoters obtained from the *E. coli* lac operon, *Streptomyces coelicolor* agarase gene (dagA), *Bacillus subtilis* levansucranse gene (sacB), *Bacillus licheniformis* alpha-amylase gene (amyl), *Bacillus stearothermophilus* maltogenic amylase gene (amyM),

*Bacillus amyloliquefaciens* alpha-amylase gene (amyQ), *Bacillus subtilis* xylA and xylB genes and prokaryotic β-lactamase gene.

An expression vector optionally contains a ribosome binding site for translation initiation, and a transcription terminator, such as PinII. The vector also optionally includes appropriate sequences for amplifying expression, e.g., an enhancer.

In addition, expression vectors of the present invention optionally contain one or more selectable marker genes to provide a phenotypic trait for selection of transformed host cells. Suitable marker genes include those coding for antibiotic resistance such as, ampicillin (ampR), kanamycin, chloramphenicol, or tetracycline resistance. Further examples include the antibiotic spectinomycin or streptomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance. Additional selectable marker genes include dihydrofolate reductase or neomycin resistance for eukaryotic cell culture, and tetracycline or ampicillin resistance in *E. coli*.

An exemplary expression vector for the expression of β-glucosidase polypeptides of the invention is described in Example 3, hereinbelow.

Synthesis And Manipulation of β-Glucosidase Polynucleotides

Polynucleotides encoding β-glucosidase can be prepared using methods that are well known in the art. Typically, oligonucleotides of up to about 40 bases are individually synthesized, then joined (e.g., by enzymatic or chemical ligation methods, or polymerase-mediated methods) to form essentially any desired continuous sequence. For example, polynucleotides of the present invention can be prepared by chemical synthesis using, for example, the classical phosphoramidite method described by Beaucage, at al., 1981, *Tetrahedron Letters,* 22:1859-69, or the method described by Matthes, et al., 1984, *EMBO J.* 3:801-05, both of which are incorporated herein by reference. These methods are typically practiced in automated synthetic methods. According to the phosphoramidite method, oligonucleotides are synthesized, e.g., in an automatic DNA synthesizer, purified, annealed, ligated and cloned in appropriate vectors.

In addition, essentially any nucleic acid can be custom ordered from any of a variety of commercial sources, such as The Midland Certified Reagent Company (Midland, Tex.), The Great American Gene Company (Ramona, Calif.), ExpressGen Inc. (Chicago, Ill.), Operon Technologies Inc. (Alameda, Calif.), and many others.

Polynucleotides may also be synthesized by well-known techniques as described in the technical literature. See, e.g., Carruthers, at al., 1982, *Cold Spring Harbor Symp. Quant. Biol.,* 47:411-18 and Adams at al., 1983, *J. Am. Chem. Soc.* 105:661, both of which are incorporated herein by reference. Double stranded DNA fragments may then be obtained either by synthesizing the complementary strand and annealing the strands together under appropriate conditions, or by adding the complementary strand using DNA polymerase with an appropriate primer sequence.

General texts that describe molecular biological techniques which are useful herein, including the use of vectors, promoters, protocols sufficient to direct persons of skill through in vitro amplification methods, including the polymerase chain reaction (PCR) and the ligase chain reaction (LCR), and many other relevant methods, include Berger and Kimmel, *Guide to Molecular Cloning Techniques, Methods in Enzymology* volume 152 Academic Press, Inc., San Diego, CA (Berger); Sambrook et al., *Molecular Cloning—A Laboratory Manual* (2nd Ed.), Vol. 1-3, Cold Spring Harbor Laboratory, Cold Spring Harbor, N.Y., 1989 ("Sambrook") and *Current Protocols in Molecular Biology*, F.M. Ausubel at al., eds., Current Protocols, a joint venture between Greene Publishing Associates, Inc. and John Wiley & Sons, Inc., (supplemented through 1999) ("Ausubel"), all of which are incorporated herein by reference. Reference is made to Berger, Sambrook, and Ausubel, as well as Mullis at al., (1987) U.S. Pat. No. 4,683,202; *PCR Protocols A Guide to Methods and Applications* (Innis at al. eds) Academic Press Inc. San Diego, Calif. (1990) (Innis); Arnheim & Levinson (Oct. 1, 1990) *C&EN* 36-47; *The Journal Of NIH Research* (1991) 3, 81-94; (Kwoh et al. (1989) *Proc. Natl. Acad. Sci. USA* 86, 1173; Guatelli et al. (1990) *Proc. Natl. Acad. Sci. USA* 87, 1874; Lomeli et al. (1989) *J. Clin. Chem* 35, 1826; Landegren at al., (1988) *Science* 241, 1077-1080; Van Brunt (1990) *Biotechnology* 8, 291-294; Wu and Wallace, (1989) *Gene* 4, 560; Barringer et al. (1990) *Gene* 89, 117, and Sooknanan and Malek (1995) *Biotechnology* 13: 563-564, all of which are incorporated herein by reference. Methods for cloning in vitro amplified nucleic acids are described in Wallace et al., U.S. Pat. No. 5,426,039, which is incorporated herein by reference.

Expression Hosts

The present invention also provides engineered (recombinant) host cells that are transformed with an expression vector or DNA construct encoding β-glucosidase. Optionally β-glucosidase expression in the cell is under the control of a heterologous promoter. Host cells of the invention may be used to produce β-glucosidase polypeptides. Thus, the present invention is directed to a host cell comprising any β-glucosidase polynucleotide of the present invention that is described hereinabove. As used herein, a genetically modified or recombinant host cell includes the progeny of said host cell that comprises a β-glucosidase polynucleotide which encodes a recombinant polypeptide of the invention. In some embodiments, the genetically modified or recombinant host cell is a eukaryotic cell. Suitable eukaryotic host cells include, but are not limited to, fungal cells, algal cells, insect cells, and plant cells. In some cases host cells may be modified to increase protein expression, secretion or stability, or to confer other desired characteristics. Cells (e.g., fungi) that have been mutated or selected to have low protease activity are particularly useful for expression. For example, C1 strains in which the alp1 (alkaline protease) locus has been deleted or disrupted may be used.

Suitable fungal host cells include, but are not limited to, Ascomycota, Basidiomycota, Deuteromycota, Zygomycota, Fungi imperfecti. Particularly preferred fungal host cells are yeast cells and filamentous fungal cells. The filamentous fungal host cells of the present invention include all filamentous forms of the subdivision Eumycotina and Oomycota. (see, for example, Hawksworth et al., In Ainsworth and Bisby's Dictionary of The Fungi, 8$^{th}$ edition, 1995, CAB International, University Press, Cambridge, UK, which is incorporated herein by reference). Filamentous fungi are characterized by a vegetative mycelium with a cell wall composed of chitin, cellulose and other complex polysaccharides. The filamentous fungal host cells of the present invention are morphologically distinct from yeast.

In one embodiment the host cell is a C1 cell. In one embodiment the host cell is a cell of a *Myceliophthora* species, such as *Myceliophthora thermophila*. In some embodiments the filamentous fungal host cell may be a cell of a species of, but not limited to *Achlya, Acremonium, Aspergillus, Aureobasidium, Bjerkandera, Ceriporiopsis, Cephalosporium, Chry-* sosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora, Mucor, Neurospora, Penicillium, Podospora, Phiebia, Piromyces, Pyricularia, Rhizomucor, Rhizopus, Schizophyllum, Scytalidium, Sporotrichum, Talaromyces, Thermoascus, Thielavia, Trametes, Tolypocladium, Trichoderma, Verticillium, Volvariella, or teleomorphs, or anamorphs, and synonyms or taxonomic equivalents thereof. In some embodiments the host cell is other than a C1 cell or is other than a Myceliophthora species.

In some embodiments of the invention, the filamentous fungal host cell is of the *Aspergillus* species, *Ceriporiopsis* species, *Chrysosporium* species, *Corynascus* species, *Fusarium* species, *Humicola* species, *Neurospora* species, *Penicillium* species, *Tolypocladium* species, *Tramates* species, or *Trichoderma* species.

In some embodiments of the invention, the filamentous fungal host cell is of the *Trichoderma* species, e.g., *T. longibrachiatum*, *T. viride* (e.g., ATCC 32098 and 32086), *Hypocrea jecorina* or *T. reesei* (NRRL 15709, ATTC 13631, 56764, 56765, 56466, 56767 and RL-P37 and derivatives thereof—See Sheir-Neiss et al., 1984, *Appl. Microbiol. Biotechnology*, 20:46-53, which is incorporated herein by reference), *T. koningii*, and *T. harzianum*. In addition, the term "Trichoderma" refers to any fungal strain that was previously classified as *Trichoderma* or currently classified as *Trichoderma*.

In some embodiments of the invention, the filamentous fungal host cell is of the *Aspergillus* species, e.g., *A. awamori*, *A. funigatus*, *A. japonicus*, *A. nidulans*, *A. niger*, *A. aculeatus*, *A. foetidus*, *A. oryzae*, *A. sojae*, and *A. kawachi*. (Reference is made to Kelly and Hynes, 1985, *EMBO J.* 4,475479; NRRL 3112, ATCC 11490, 22342, 44733, and 14331; Yelton et al., 1984, *Proc. Natl. Acad. Sci. USA*, 81, 1470-1474; Tilburn et al., 1982, *Gene* 26, 205-221; and Johnston et al., 1985, *EMBO J.* 4, 1307-1311, all of which are incorporated herein by reference).

In some embodiments of the invention, the filamentous fungal host cell is of the *Fusarium* species, e.g., *F. bactridioides*, *F. cerealis*, *F. crookwellense*, *F. culmorum*, *F. graminearum*, *F. graminum*, *F. oxysporum*, *F. roseum*, and *F. venenatum*. In some embodiments of the invention, the filamentous fungal host cell is of the *Neurospora* species, e.g., *N. crassa*. Reference is made to Case, M.E. et al., (1979) *Proc. Natl. Acad. Sci.* USA, 76, 5259-5263; U.S. Pat. No. 4,486,553; and Kinsey, J. A. and J. A. Rambosek (1984) *Molecular and Cellular Biology* 4, 117-122, all of which are incorporated herein by reference. In some embodiments of the invention, the filamentous fungal host cell is of the *Humicola* species, e.g., *H. insolens*, *H. grisea*, and *H. lanuginosa*. In some embodiments of the invention, the filamentous fungal host cell is of the *Mucor* species, e.g., *M. miehei* and *M. circinelloides*. In some embodiments of the invention, the filamentous fungal host cell is of the *Rhizopus* species, e.g., *R. oryzae* and *R. niveus*. In some embodiments of the invention, the filamentous fungal host cell is of the *Penicillum* species, e.g., *P. purpurogenum*, *P. chrysogenum*, and *P. verruculosum*. In some embodiments of the invention, the filamentous fungal host cell is of the *Thielavia* species, e.g., *T. terrestris*. In some embodiments of the invention, the filamentous fungal host cell is of the *Tolypocladium* species, e.g., *T. inflatum* and *T. geodes*. In some embodiments of the invention, the filamentous fungal host cell is of the *Trametes* species, e.g., *T. villosa* and *T. versicolor*.

In some embodiments of the invention, the filamentous fungal host cell is of the *Chrysosporium* species, e.g., *C. lucknowense*, *C. keratinophilum*, *C. tropicum*, *C. merdarium*, *C. Mops*, *C. pannicola*, and *C. zonatum*. In a particular embodiment the host is *C. lucknowense*.

In the present invention a yeast host cell may be a cell of a species of, but not limited to *Candida*, *Hansenula*, *Saccharomyces*, *Schizosaccharomyces*, *Pichia*, *Kluyveromyces*, and *Yarrowia*. In some embodiments of the invention, the yeast cell is *Hansenula polymorpha*, *Saccharomyces cerevisiae*, *Saccharomyces carlsbergensis*, *Saccharomyces diastaticus*, *Saccharomyces norbensis*, *Saccharomyces kluyveri*, *Schizosaccharomyces pombe*, *Pichia pastoris*, *Pichia finlandica*, *Pichia trehalophila*, *Pichia kodamae*, *Pichia membranaefaciens*, *Pichia opuntiae*, *Pichia thermotolerans*, *Pichia salictaria*, *Pichia quercuum*, *Pichia pijperi*, *Pichia stipitis*, *Pichia methanolica*, *Pichia angusta*, *Kluyveromyces lactis*, *Candida albicans*, and *Yarrowia lipolytica*.

In some embodiments on the invention, the host cell is an algal such as, *Chlamydomonas* (e.g., *C. Reinhardtii*) and *Phormidium* (*P.* sp. ATCC29409).

In other embodiments, the host cell is a prokaryotic cell. Suitable prokaryotic cells include gram positive, gram negative and gram-variable bacterial cells. The host cell may be a species of, but not limited to *Agrobacterium*, *Alicyclobacillus*, *Anabaena*, *Anacystis*, *Acinetobacter*, *Acidothermus*, *Arthrobacter*, *Azobacter*, *Bacillus*, *Bifidobacterium*, *Brevibacterium*, *Butyrivibrio*, *Buchnera*, *Campestris*, *Camplyobacter*, *Clostridium*, *Corynebacterium*, *Chromatium*, *Coprococcus*, *Escherichia*, *Enterococcus*, *Enterobacter*, *Erwinia*, *Fusobacterium*, *Faecalibacterium*, *Francisella*, *Flavobacterium*, *Geobacillus*, *Haemophilus*, *Helicobacter*, *Klebsiella*, *Lactobacillus*, *Lactococcus*, *Ilyobacter*, *Micrococcus*, *Microbacterium*, *Mesorhizobium*, *Methylobacterium*, *Methylobacterium*, *Mycobacterium*, *Neisseria*, *Pantoea*, *Pseudomonas*, *Prochlorococcus*, *Rhodobacter*, *Rhodopseudomonas*, *Rhodopseudomonas*, *Roseburia*, *Rhodospirillum*, *Rhodococcus*, *Scenedesmus*, *Streptomyces*, *Streptococcus*, *Synecoccus*, *Saccharomonospora*, *Staphylococcus*, *Serratia*, *Salmonella*, *Shigella*, *Thermoanaerobacterium*, *Tropheryma*, *Tularensis*, *Temecula*, *Thermosynechococcus*, *Thermococcus*, *Ureaplasma*, *Xanthomonas*, *Xylella*, *Yersinia* and *Zymomonas*.

In some embodiments, the host cell is a species of *Agrobacterium*, *Acinetobacter*, *Azobacter*, *Bacillus*, *Bifidobacterium*, *Buchnera*, *Geobacillus*, *Campylobacter*, *Clostridium*, *Corynebacterium*, *Escherichia*, *Enterococcus*, *Erwinia*, *Flavobacterium*, *Lactobacillus*, *Lactococcus*, *Pantoea*, *Pseudomonas*, *Staphylococcus*, *Salmonella*, *Streptococcus*, *Streptomyces*, and *Zymomonas*.

In yet other embodiments, the bacterial host strain is non-pathogenic to humans. In some embodiments the bacterial host strain is an industrial strain. Numerous bacterial industrial strains are known and suitable in the present invention.

In some embodiments of the invention the bacterial host cell is of the *Agrobacterium* species, e.g., *A. radiobacter*, *A. rhizogenes*, and *A. rubi*. In some embodiments of the invention the bacterial host cell is of the *Arthrobacter* species, e.g., *A. aurescens*, *A. citreus*, *A. globformis*, *A. hydrocarboglutamicus*, *A. mysorens*, *A. nicotianae*, *A. paraffineus*, *A. protophonniae*, *A. roseoparqffinus*, *A. sulfureus*, and *A. ureafaciens*. In some embodiments of the invention the bacterial host cell is of the *Bacillus* species, e.g., *B. thuringiensis*, *B. anthracis*, *B. megaterium*, *B. subtilis*, *B. lentus*, *B. circulans*, *B. pumilus*, *B. lautus*, *B. coagulans*, *B. brevis*, *B. firmus*, *B. alkaophius*, *B. licheniformis*, *B. clausii*, *B. stearothermophilus*, *B. halodurans* and *B. amyloliquefaciens*. In particular embodiments, the host cell will be an industrial *Bacillus* strain including but not limited to *B. subtilis*, *B. pumilus*, *B. licheniformis*, *B. megaterium*, *B. clausii*, *B. stearothermophi-*

*lus* and *B. amyloliquefaciens*. Some preferred embodiments of a *Bacillus* host cell include *B. subtilis, B. licheniformis, B. megaterium, B. stearothermophilus* and *B. amyloliquefaciens*. In some embodiments the bacterial host cell is of the *Clostridium* species, e.g., *C. acetobutylicum, C. tetani* E88, *C. lituseburense, C. saccharobutylicum, C. perfringens,* and *C. beijerinckii*. In some embodiments the bacterial host cell is of the Corynebacterium species e.g., *C. glutamicum* and *C. acetoacidophilum*. In some embodiments the bacterial host cell is of the *Escherichia* species, e.g., *E. coli*. In some embodiments the bacterial host cell is of the *Erwinia* species, e.g., *E. uredovora, E. carotovora, E. ananas, E. herbicola, E. punctata,* and *E. terreus*. In some embodiments the bacterial host cell is of the *Pantoea* species, e.g., *P. citrea,* and *P. agglomerans*. In some embodiments the bacterial host cell is of the *Pseudomonas* species, e.g., *P. putida, P. aeruginosa, P. mevalonii,* and *P.* sp. D-0I 10. In some embodiments the bacterial host cell is of the *Streptococcus* species, e.g., *S. equisimiles, S. pyogenes,* and *S. uberis*. In some embodiments the bacterial host cell is of the *Streptomyces* species, e.g., *S. ambofaciens, S. achromogenes, S. avermitilis, S. coelicolor, S. aureofaciens, S. aureus, S. fungicidicus, S. griseus,* and *S. lividans*. In some embodiments the bacterial host cell is of the *Zymomonas* species, e.g., *Z. mobilis,* and *Z. lipolytica*.

Strains that may be used in the practice of the invention including both prokaryotic and eukaryotic strains, are readily accessible to the public from a number of culture collections such as American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Host cells may be genetically modified to have characteristics that improve protein secretion, protein stability or other properties desirable for expression and/or secretion of a protein. Genetic modification can be achieved by genetic engineering techniques or using classical microbiological techniques, such as chemical or UV mutagenesis and subsequent selection. A combination of recombinant modification and classical selection techniques may be used to produce the organism of interest. Using recombinant technology, nucleic acid molecules can be introduced, deleted, inhibited or modified, in a manner that results in increased yields of β-glucosidase within the organism or in the culture. For example, knock out of Alp1 function results in a cell that does not express most or all cellulases. Knock out of pyr5 function results in a cell with a pyrimidine deficient phenotype.

Transformation

Introduction of a vector or DNA construct into a host cell can be effected by calcium phosphate transfection, DEAE-Dextran mediated transfection, electroporation, or other common techniques (See Davis et al., 1986, *Basic Methods in Molecular Biology*, which is incorporated herein by reference). One method for transformation of C1 host cells is described in Example 4, below. Transformation of C1 host cells is known in the art (see, e.g., US 2008/0194005 which is incorporated herein by reference).

Culture Conditions

The engineered host cells can be cultured in conventional nutrient media modified as appropriate for activating promoters, selecting transformants, or amplifying the β-glucosidase polynucleotide. Culture conditions, such as temperature, pH and the like, are those previously used with the host cell selected for expression, and will be apparent to those skilled in the art. As noted, many references are available for the culture and production of many cells, including cells of bacterial, plant, animal (especially mammalian) and archebacterial origin. See e.g., Sambrook, Ausubel, and Berger (all supra), as well as Freshney (1994) *Culture of Animal Cells, a Manual of Basic Technique,* third edition, Wiley-Liss, New York and the references cited therein; Doyle and Griffiths (1997) *Mammalian Cell Culture: Essential Techniques* John Wiley and Sons, NY; Humason (1979) *Animal Tissue Techniques,* fourth edition W.H. Freeman and Company; and Ricciardelli, et al., (1989) *In vitro Cell Dev. Biol.* 25:1016-1024, all of which are incorporated herein by reference. For plant cell culture and regeneration, Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture;* Fundamental Methods Springer Lab Manual, Springer-Verlag (Berlin Heidelberg New York); Jones, ed. (1984) *Plant Gene Transfer and Expression Protocols,* Humana Press, Totowa, N.J. and *Plant Molecular Biology* (1993) R. R. D. Croy, Ed. Bios Scientific Publishers, Oxford, U.K. ISBN 0 12 198370 6, all of which are incorporated herein by reference. Cell culture media in general are set forth in Atlas and Parks (eds.) *The Handbook of Microbiological Media* (1993) CRC Press, Boca Raton, Fla., which is incorporated herein by reference. Additional information for cell culture is found in available commercial literature such as the *Life Science Research Cell Culture Catalogue* (1998) from Sigma-Aldrich, Inc (St Louis, Mo.) ("Sigma-LSRCCC") and, for example, *The Plant Culture Catalogue* and supplement (1997) also from Sigma-Aldrich, Inc (St Louis, Mo.) ("Sigma-PCCS"), all of which are incorporated herein by reference.

Culture conditions for C1 host cells are known in the art and can be readily determined by one of skill. See, e.g., US 2008/0194005, US 20030187243, WO 2008/073914 and WO 01/79507, which are incorporated herein by reference.

In some embodiments, cells expressing the β-glucosidase polypeptides of the invention are grown under batch or continuous fermentations conditions. Classical batch fermentation is a closed system, wherein the compositions of the medium is set at the beginning of the fermentation and is not subject to artificial alternations during the fermentation. A variation of the batch system is a fed-batch fermentation which also finds use in the present invention. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth. Continuous fermentation systems strive to maintain steady state growth conditions. Methods for modulating nutrients and growth factors for continuous fermentation processes as well as techniques for maximizing the rate of product formation are well known in the art of industrial microbiology.

Cell-free transcription/translation systems can also be employed to produce β-glucosidase polypeptides using the polynucleotides of the present invention. Several such systems are commercially available. A general guide to in vitro transcription and translation protocols is found in Tymms (1995) *In vitro Transcription and Translation Protocols: Methods in Molecular Biology,* Volume 37, Garland Publishing, NY, which is incorporated herein by reference.

V. Production And Recovery of B-Glucosidase Polypeptides

The present invention is directed to a method of making a polypeptide having β-glucosidase activity, the method comprising providing a host cell transformed with any one of the described β-glucosidase polynucleotides of the present invention; culturing the transformed host cell in a culture medium under conditions in which the host cell expresses the encoded β-glucosidase polypeptide; and optionally recovering or isolating the expressed β-glucosidase polypeptide, or recovering or isolating the culture medium containing the expressed β-glucosidase polypeptide. The method further provides optionally lysing the transformed host cells after expressing the encoded β-glucosidase polypeptide and optionally recovering or isolating the expressed β-glucosidase polypeptide from the cell lysate. The present invention further provides a method of making a β-glucosidase polypeptide, said method comprising cultivating a host cell transformed with a β-glucosidase polynucleotide under conditions suitable for the production of the β-glucosidase polypeptide and recovering the β-glucosidase polypeptide. In a further embodiment, the present invention provides a method of over-expressing (i.e., making) a C1 β-glucosidase polypeptide comprising: (a) providing a recombinant C1 host cell comprising a nucleic acid construct, wherein the nucleic acid construct comprises a polynucleotide sequence that encodes a mature C1 β-glucosidase of the present invention and the nucleic acid construct optionally also comprises a polynucleotide sequence encoding a signal peptide at the amino terminus of said mature β-glucosidase, wherein the polynucleotide sequence encoding the mature C1β-glucosidase and optional signal peptide is operably linked to a heterologous promoter; and (b) culturing the host cell in a culture medium under conditions in which the host cell expresses the encoded β-glucosidase polypeptide, wherein the level of expression of β-glucosidase from the host cell is at least about 2-fold greater than that from wildtype C1 cultured under the same conditions. β-glucosidase polypeptide expression may be measured using a para-nitrophenyl-β-D-glucopyranoside (pNPG) β-glucosidase activity assay, such as that described in Example 5. Expression (i.e., activity) of secreted β-glucosidase may be measured. Alternatively expression of total β-glucosidase acitvity in the culture may be determined. The signal peptide employed in this method may be any heterologous signal peptide known in the art or may be the wildtype C1 β-glucosidase signal peptide (SEQ ID NO:6). In some embodiments, the level of overexpression is at least about 5-fold, 10-fold, 12-fold, 15-fold, 20-fold, 25-fold, 30-fold, or 35-fold greater than expression of β-glucosidase from wildtype C1.

Typically, recovery or isolation of the β-glucosidase polypeptide is from the host cell culture medium, the host cell or both, using protein recovery techniques that are well known in the art, including those described herein. Cells are typically harvested by centrifugation, disrupted by physical or chemical means, and the resulting crude extract may be retained for further purification. Microbial cells employed in expression of proteins can be disrupted by any convenient method, including freeze-thaw cycling, sonication, mechanical disruption, or use of cell lysing agents, or other methods, which are well known to those skilled in the art.

The resulting polypeptide may be recovered/isolated and optionally purified by any of a number of methods known in the art. For example, the polypeptide may be isolated from the nutrient medium by conventional procedures including, but not limited to, centrifugation, filtration, extraction, spray-drying, evaporation, chromatography (e.g., ion exchange, affinity, hydrophobic interaction, chromatofocusing, and size exclusion), or precipitation. Protein refolding steps can be used, as desired, in completing the configuration of the mature protein. Finally, high performance liquid chromatography (HPLC) can be employed in the final purification steps. Purification of BGL1 is described in US patent publication U.S. 2007/0238155, incorporated herein by reference. In addition to the references noted supra, a variety of purification methods are well known in the art, including, for example, those set forth in Sandana (1997) *Bioseparation of Proteins,* Academic Press, Inc.; Bollag at al. (1996) *Protein Methods,* 2$^{nd}$ Edition, Wiley-Liss, NY; Walker (1996) *The Protein Protocols Handbook* Humana Press, NJ; Harris and Angal (1990) *Protein Purification Applications: A Practical Approach,* IRL Press at Oxford, Oxford, England; Harris and Angal *Protein Purification Methods: A Practical Approach,* IRL Press at Oxford, Oxford, England; Scopes (1993) *Protein Purification: Principles and Practice* 3$^{rd}$ Edition, Springer Verlag, NY; Janson and Ryden (1998) *Protein Purification: Principles, High Resolution Methods and Applications,* Second Edition, Wiley-VCH, NY; and Walker (1998) *Protein Protocols on CD-ROM,* Humana Press, NJ, all of which are incorporated herein by reference. In some cases, the purified protein may be purified to near homogeneity or may constitute at least 20%, at least 30% or at least 50% of the protein in the composition.

Immunological methods may be used to purify β-glucosidase polypeptides. In one approach antibody raised against the β-glucosidase polypeptides (e.g., against a polypeptide comprising SEQ ID NO:5) using conventional methods is immobilized on beads, mixed with cell culture media under conditions in which the β-glucosidase is bound, and precipitated. In a related approach immunochromatograpy is used.

As noted, in some embodiments the β-glucosidase is expressed as a fusion protein including a non-enzyme portion. In some embodiments the β-glucosidase sequence is fused to a purification facilitating domain. As used herein, the term "purification facilitating domain" refers to a domain that mediates purification of the polypeptide to which it is fused. Suitable purification domains include metal chelating peptides, histidine-tryptophan modules that allow purification on immobilized metals, a sequence which binds glutathione (e.g., GST), a hemagglutinin (HA) tag (corresponding to an epitope derived from the influenza hemagglutinin protein; Wilson et al. (1984) Cell, 37:767), maltose binding protein sequences, the FLAG epitope utilized in the FLAGS extension/affinity purification system (Immunex Corp, Seattle, Wash.), and the like. The inclusion of a protease-cleavable polypeptide linker sequence between the purification domain and the HHDH polypeptide is useful to facilitate purification. One expression vector contemplated for use in the compositions and methods described herein provides for expression of a fusion protein comprising a polypeptide of the invention fused to a polyhistidine region separated by an enterokinase cleavage site. The histidine residues facilitate purification on IMIAC (immobilized metal ion affinity chromatography, as described in Porath et al. (1992) *Protein Expression and Purification* 3:263-281) while the enterokinase cleavage site provides a means for separating the HHDH polypeptide from the fusion protein. pGEX vectors (Promega; Madison, Wis.) may also be used to express foreign polypeptides as fusion proteins with glutathione S-transferase (GST). In general, such fusion proteins are soluble and can easily be purified from lysed cells by adsorption to ligand-agarose beads (e.g., glutathione-agarose in the case of GST-fusions) followed by elution in the presence of free ligand.

VI. Methods of Using B-Glucosidase Polypeptides And Cells Expressing B-Glucosidase Polypeptides As described supra, β-glucosidase polypeptides of the present invention can be used to catalyze the hydrolysis of a sugar dimer with the release of the corresponding sugar monomer, for example the conversion of cellobiose with the release of glucose. Thus, the present invention provides a method for producing glucose, by (a) providing a cellobiose; and (b) contacting the cellobiose with a β-glucosidase polypeptide of the invention under conditions sufficient to form a reaction mixture for converting the cellobiose to glucose. The β-glucosidase polypeptide may be utilized in such methods in either isolated form or as part of a composition, such as any of those described herein. The β-glucosidase polypeptide may also be provided in cell culturing media or in a cell lysate. For example, after producing the β-glucosidase polypeptide by culturing a host cell transformed with a β-glucosidase polynucleotide or vector of the present invention, the β-glucosidase need not be isolated from the culture medium (i.e., if the β-glucosidase is secreted into the culture medium) or cell lysate (i.e., if the β-glucosidase is not secreted into the culture medium) or used in purified form to be useful in further methods of using the β-glucosidase polypeptide. Any composition, cell culture medium, or cell lysate containing a β-glucosidase polypeptide of the present invention may be suitable for using in methods that utilize a β-glucosidase. Therefore, the present invention further provides a method for producing glucose, by: (a) providing a cellobiose; and (b) contacting the cellobiose with a culture medium or cell lysate or composition comprising a β-glucosidase polypeptide of the present invention under conditions sufficient to form a reaction mixture for converting the cellobiose to glucose.

The present invention further provides compositions that are useful for the enzymatic conversion of cellobiose to glucose. For example, one or more β-glucosidase polypeptides of the present invention may be combined with another enzyme and/or an agent that alters the bulk material handling properties or further processability of the glucosidase(s) (e.g., a flow aid agent, water, buffer, a surfactant, and the like) or that improves the efficiency of the conversion of cellobiose to glucose, as described in more detail hereinbelow. The other enzyme may be a different β-glucosidase or another cellulase enzyme.

Cellulase Mixtures

For example, in some embodiments, the β-glucosidase is combined with other cellulases to form a cellulase mixture. The cellulase mixture may include cellulases selected from CBH, EG and BG cellulases (e.g., cellulases from *Trichoderma reesei* (e.g., C2730 Cellulase from *Trichoderma reesei* ATCC No. 25921, Sigma-Aldrich, Inc.), *Acidothermus cellulolyticus, Thermobifida fusca, Humicola grisea* and *Chrysosporium* sp.). The enzymes of the cellulase mixture work together resulting in decrystallization and hydrolysis of the cellulose from a biomass substrate to yield soluble sugars, such as but not limited to glucose (See Brigham et al., 1995, in Handbook on Bioethanol (C. Wyman ed.) pp 119-141, Taylor and Francis, Washington D.C., which is incorporated herein by reference).

Cellulase mixtures for efficient enzymatic hydrolysis of cellulose are known (see, e.g., Viikari et al., 2007, "Thermostable enzymes in lignocellulose hydrolysis" *Adv Biochem Eng Biotechnol* 108:121-45, and US Pat. publications U.S. 2009/0061484; U.S. 2008/0057541; and U.S. 2009/0209009 to Iogen Energy Corp.), each of which is incorporated herein by reference for all purposes. In some embodiments, mixtures of purified naturally occurring or recombinant enzymes are combined with cellulosic feedstock or a product of cellulose hydrolysis. Alternatively or in addition, one or more cells producing naturally occurring or recombinant cellulases may be used.

Other Components of β-Glucosidase Compositions

β-glucosidase polypeptides of the present invention may be used in combination with other optional ingredients such as a buffer, a surfactant, and/or a scouring agent. A buffer may be used with a β-glucosidase polypeptide of the present invention (optionally combined with other cellulases, including another β-glucosidase) to maintain a desired pH within the solution in which the β-glucosidase is employed. The exact concentration of buffer employed will depend on several factors which the skilled artisan can determine. Suitable buffers are well known in the art. A surfactant may further be used in combination with the cellulases of the present invention. Suitable surfactants include any surfactant compatible with the β-glucosidase and optional other cellulases being utilized. Exemplary surfactants include an anionic, a nonionic, and ampholytic surfactants.

Suitable anionic surfactants include, but are not limited to, linear or branched alkylbenzenesulfonates; alkyl or alkenyl ether sulfates having linear or branched alkyl groups or alkenyl groups; alkyl or alkenyl sulfates; olefinsulfonates; alkanesulfonates, and the like. Suitable counter ions for anionic surfactants include, for example, alkali metal ions, such as sodium and potassium; alkaline earth metal ions, such as calcium and magnesium; ammonium ion; and alkanolamines having from 1 to 3 alkanol groups of carbon number 2 or 3. Ampholytic surfactants suitable for use in the practice of the present invention include, for example, quaternary ammonium salt sulfonates, betaine-type ampholytic surfactants, and the like. Suitable nonionic surfactants generally include polyoxyalkylene ethers, as well as higher fatty acid alkanolamides or alkylene oxide adduct thereof, fatty acid glycerine monoesters, and the like. Mixtures of surfactants can also be employed as is known in the art.

Production of Fermentable Sugars From Cellulosic Biomass

β-glucosidase polypeptides of the present invention, as well as any composition, culture medium, or cell lysate comprising such β-glucosidase polypeptides, may be used in the production of monosaccharides, disaccharides, or oligomers of a mono- or di-saccharide as chemical or fermentation feedstock from biomass. As used herein, the term "biomass" refers to living or dead biological material that contains a polysaccharide substrate, such as, for example, cellulose, starch, and the like. Therefore, the present invention provides a method of converting a biomass substrate to a fermentable sugar, the method comprising contacting a culture medium or cell lysate containing a β-glucosidase polypeptide according to the invention, with the biomass substrate under conditions suitable for the production of the fermentable sugar. The present invention further provides a method of converting a biomass substrate to a fermentable sugar by (a) pretreating a cellulose substrate to increase its susceptibility to hydrolysis; (b) contacting the pretreated cellulose substrate of step (a) with a composition, culture medium or cell lysate containing a β-glucosidase polypeptide of the present invention (and optionally other cellulases) under conditions suitable for the production of the fermentable sugar.

In some embodiments, the biomass includes cellulosic substrates including but not limited to, wood, wood pulp, paper pulp, corn stover, corn fiber, rice, paper and pulp processing waste, woody or herbaceous plants, fruit or vegetable pulp, distillers grain, grasses, rice hulls, wheat straw, cotton, hemp, flax, sisal, corn cobs, sugar cane bagasse, switch grass and mixtures thereof. The biomass may optionally be pretreated to increase the susceptibility of cellulose to hydrolysis using methods known in the art such as chemical, physical and biological pretreatments (e.g., steam explosion, pulping, grinding, acid hydrolysis, solvent exposure, and the like, as well as combinations thereof). In some embodiments, the biomass comprises transgenic plants that express ligninase and/or cellulase enzymes which degrade lignin and cellulose. See, e.g., U.S. 20080104724, which is incorporated herein by reference. The biomass may include cellobiose and/or may be treated enzymatically to generate cellobiose for conversion to a soluable sugar (e.g., glucose).

In some embodiments, the β-glucosidase polypeptide and β-glucosidase polypeptide-containing compositions, cell culture media, and cell lysates may be reacted with the biomass or pretreated biomass at a temperature in the range of about 25° C. to about 100° C., about 30° C. to about 90° C., about 30° C. to about 80° C., about 40° C. to about 80° C. and about 35° C. to about 75° C. Also the biomass may be reacted with the β-glucosidase polypeptides and β-glucosidase polypeptide-containing compositions, cell culture media, and cell lysates at a temperature about 25° C., at about 30° C., at about 35° C., at about 40° C., at about 45° C., at about 50° C., at about 55° C., at about 60° C., at about 65° C., at about 70° C., at about 75° C., at about 80° C., at about 85° C., at about 90° C., at about 95° C. and at about 100° C. In addition to the temperatures described above, conditions suitable for converting a biomass substrate to a fermentable sugar that employ a β-glucosidase polypeptide of the present invention (optionally in a composition, cell culture medium, or cell lysate) include carrying out the process at a pH in a range from about pH 3.0 to about 8.5, about pH 3.5 to about 8.5, about pH 4.0 to about 7.5, about pH 4.0 to about 7.0 and about pH 4.0 to about 6.5. Those having ordinary skill in the art will appreciate that the reaction times for converting a particular biomass substrate to a fermentable sugar may vary but the optimal reaction time can be readily determined. Exemplary reaction times may be in the range of from about 1.0 to about 240 hours, from about 5.0 to about 180 hrs and from about 10.0 to about 150 hrs. For example, the incubation time may be at least 1 hr, at least 5 hrs, at least 10 hrs, at least 15 hrs, at least 25 hrs, at least 50 hr, at least 100 hrs, at least 180 and the like.

Reaction of the β-glucosidase with biomass substrate or pretreated biomass substrate under these conditions may result in the release of substantial amounts of the soluble sugars from the substrate. For example at least 20%, at least 30%, at least 40%, at least 50%, at least 60%, at least 70%, at least 80%, at least 90% or more soluble sugar may be available as compared to the release of sugar by the wildtype C1. In some embodiment the amount of soluble sugar made available may be at least 2-fold, at least 3-fold, at least 4-fold, or at least 5-fold greater than that made available by the wildtype C1 under the same conditions. In some embodiments, the soluble sugars will comprise glucose.

The soluble sugars produced by the methods of the present invention may be used to produce an alcohol (such as, for example, ethanol, butanol, and the like). The present invention therefore provides a method of producing an alcohol, where the method comprises (a) providing a fermentable sugar produced using a β-glucosidase polypeptide of the present invention in the methods described supra; (b) contacting the fermentable sugar with a fermenting microorganism to produce the alcohol or other metabolic product; and (c) recovering the alcohol or other metabolic product.

In some embodiments, the β-glucosidase polypeptide of the present invention, or composition, cell culture medium, or cell lysate containing the β-glucosidase polypeptide may be used to catalyze the hydrolysis of a biomass substrate to a fermentable sugar in the presence of a fermenting microorganism such as a yeast (e.g., Saccharomyces sp., such as, for example, *S. cerevisiae, Zymomonas* sp., *E. coli, Pichia* sp., and the like) or other C5 or C6 fermenting microorganisms that are well known in the art, to produce an end-product such as ethanol. In this simultaneous saccharification and fermentation (SSF) process the fermentable sugars (e.g., glucose and/or xylose) are removed from the system by the fermentation process.

The soluble sugars produced by the use of a β-glucosidase polypeptide of the present invention may also be used in the production of other end-products. such as, for example, acetone, an amino acid (e.g., glycine, lysine, and the like), an organic acid (e.g., lactic acid, and the like), glycerol, a diol (e.g., 1,3 propanediol, butanediol, and the like) and animal feeds.

One of skill in the art will readily appreciate that the β-glucosidase polypeptide compositions of the present invention may be used in the form of an aqueous solution or a solid concentrate. When aqueous solutions are employed, the β-glucosidase solution can easily be diluted to allow accurate concentrations. A concentrate can be in any form recognized in the art including, for example, liquids, emulsions, suspensions, gel, pastes, granules, powders, an agglomerate, a solid disk, as well as other forms that are well known in the art. Other materials can also be used with or included in the β-glucosidase composition of the present invention as desired, including stones, pumice, fillers, solvents, enzyme activators, and anti-redeposition agents depending on the intended use of the composition.

In addition to use for conversion of cellulosic biomass, β-glucosidase polypeptides and compositions thereof may also be used in the food and beverage industry for example in the process of wine making for the efficient release of monoterpenols (see, for example, Yanai and Sato (1999) *Am. J. Enol. Eitic.,* 50:231-235, which is incorporated herein by reference) and for the preparation of glycon isoflavone-enriched tofu (see, for example, Mase et al., (2004) J. Appl. Glycosci., 51:211-216, which is incorporated herein by reference). β-glucosidase polypeptides of the present invention may also be employed in detergent compositions for improved cleaning performance (see, for example, U.S. Pat. No. 7,244,605; U.S. Pat. No. 5,648,263 and WO 2004/048592, which are incorporated herein by reference).

The foregoing and other aspects of the invention may be better understood in connection with the following non-limiting examples.

VIII. EXAMPLES

Example 1

Cloning of Genomic DNA

Genomic DNA was isolated from C1 cells using standard procedures. Briefly, hyphal innoculum was seeded into a growth medium and allowed to grow for 72 hours at 35° C. The mycelian mat was collected by centrifugation, washed, and 50 ul DNA extraction buffer (200 mM TRIS pH 8.0; 250 mM NaCl; 125 mM EDTA; 0.5% SDS) was added. The mycelium was ground with conical grinder, reextracted with 250 ul extraction buffer, and the suspension was centrifuged. The supernatant was transfered to a new tube containing 300

μl isopropanol. DNA was collected by centrifugation, washed twice with 70% ethanol, and diluted in 100 μl of water.

The region including the β-glucosidase bgl1 gene was cloned from each of three C1 strains, including wildtype cells and two different Alp1⁻ cell lines, and sequenced. Cloning was carried out using PCR with internal and external primers shown in Table 3. The amplification product of the internal primers is the protein coding portion of the bgl1 gene, while the external primer include 5' and 3' flanking sequences.

TABLE 3

Internal primers:

| C1bg1_fwd1 | ATGAAGGCTGCTGCGCTTTC | SEQ ID NO: 22 |
| C1bg1_rev1 | TCATTAAGGAAGCTCAATCT TGAGATC | SEQ ID NO: 23 |

External primers:

| C1bg1_fwd2 | TCTCTGCCGGTGCCATCAATCATCT | SEQ ID NO: 24 |
| C1bg1_rev2 | GCTCACCGGAACTTGCCAAGTGCT | SEQ ID NO: 25 |

The bgl1 sequence is provided in FIGS. 1A-F (upper sequence). Notably, the C1 genomic sequence we obtained differed from published sequences at four positions (corresponding to nucleotides 1440, 1451, 1511, and 1521 of SEQ ID NO:1).

Example 2

Cloning of cDNA

The C1 bgl1 cDNA was cloned and sequenced as described below.

RNA Extraction From C1 Fermentation Media

RNA was purified from 3 days old culture of C1 (Alp1⁻ strain) grown at 35° C. with 250 rpm shaking. 500-1200 μl of the culture broth was transferred into a cooled mortar and grinded thoroughly with the pestle in the presence of liquid N2. The cell powder was transferred into an Eppendorf tube and 1500 μl Trizol reagent was added to the sample. After mixing, it was incubated for 20 min at room temperature and centrifuged at 12000 g, 4° C., for 15 min. The clear homogenate was transferred into a 2 ml centrifuge tube and 300 μl chloroform was added, mixed and centrifuged at 12000 g 4° C. for 30 min. The upper, aqueous phase was transferred into a new 2 ml tube and precipitated by adding 1200 μl 96% EtOH. The sample was further purified using the Qiagen RNeasy Kit using manufacturer instructions. Shortly: 700 μl precipitated sample was transferred into RNeasy Mini Spin column and centrifuged for 20 sec at 10000 g at 20° C. 350 μl RW1 buffer was added and centrifuged for 20 sec at 10000 g at 20° C. The DNase solution was added directly to the RNeasy spin column membrane, and incubated at room temperature for 25 min. 350 pl RW1 buffer was added and centrifuged for 20 sec at 10000 g at 20° C. Two times 500 μl RPE buffer was added to the Spin Column and centrifuge for 20 sec at 10000 g at 20° C. The RNeasy spin column was placed in a new 2 ml collection tube and centrifuged for 1 min at 10000 g at 20° C. Then the RNeasy spin column was placed to a new 1.5 ml collection tube and 30 μl RNease-free water was directly added to the spin column membrane and centrifuged for 1 min at 10000 g at 20° C. The concentration of the total RNA solution was about 1.9 μg/ul.

First strand synthesis using Superscript III Reverse Transcriptase

Into a nuclease-free microcentrifuge tube the following components were added:

1. 5 μl of oligo(dT) (400 ng/ul) (Qiagen Cat. No. 70DT01-1)
2. 1 μg total RNA
3. 1 μl 10 mM dNTP
4. Sterile, distilled water to 13 μl The mixture was heated to 65° C. for 5 minutes and incubated on ice for 1 minute and 4 μl 5×First-Strand Buffer, 1 μl 0.1 M DTT, 1.3 μl RNaseOUT™ Recombinant RNase Inhibitor (Cat. No. 10777-019) and 2 μl of SuperScript™ III RT. The mixture was incubated at 50° C. for 60 minutes and the reaction was inactivated by heating at 70° C. for 15 minutes.

PCR Cloning of bgl1 cDNA

To clone full length cDNA of bgl1 from the RT-PCR mix, 2 μl from the RT-PCR mix, 10 μl 5×Phusion HF buffer, 1 μl dNTP (Σ10 mM), 1 μl of Primer cdx09050 (10 μM), 1 ul of Primer cdx09052 (10 μM), 34.5 ul MQ water, and 0.5 μl Phusion HF* Polymerase (Finnzymes) was added and mixed. PCR conditions were: Initial denaturation: 98° C.-30 sec, followed by 35 cycles of 98° C.-10 sec denaturation and 72° C. 2 min 40 sec elongation, and a final extension cycle of 72° C. for 5 min. The PCR product was purified with EZ-10 spin column according to the manufacturer instructions and cloned into PCRBlunt using the StrataClone Ultra Blunt PCR cloning kit (Stratagene) according to the manufacturer instructions.

TABLE 4

| Primer name | Sequence (5'-3') | SEQ ID NO: |
|---|---|---|
| cdx09050 | GGCTCATGAAGGCTGCTGCGCTTTCCTGC | 26 |
| cdx09052 | GCCGAATTCTCAAGGAAGCTCAATCTTGA GATCC | 27 |
| TcbhC1bg1_R1 | GCGTGTCTCAGAACCTCCTTCAGAGAGGT TCGTTTACTTACTTATTATCAAGGAAGCT CAATCTTGAGATCC | 28 |
| PcbhC1bg1_F | GTCTTCAGATCAAGCAACTGTGTGCTGATCC TCTTCCGTCATGAAGGCTGCTGCGCTTTC | 10 |

FIGS. 2A-D shows the cDNA sequence obtained (also see FIGS. 1A-F) along with the predicted protein sequence. As illustrated in FIG. 3, the exon structure of the bgl1 gene differs from that previously described (see patent publication US 2007/0238155). The exon structure reflected in the cDNA sequence was consistent with analysis of the corresponding genomic sequence using the Augustus v.2.03 and Genemark-ES v.2 gene prediction algorithms (see Stanke et al., 2006, "AUGUSTUS: ab initio prediction of alternative transcripts" *Nucleic Acids Res.* 34 (Web Server issue):W435-9; Ter-Hovhannisyan et al., 2008, Genome Res. 18:1979-90). As a consequence of the differences in the cDNA sequence, the BGL1 protein sequence we identified differs from the previously described sequence at the amino terminus and internally.

Because BGL1 is secreted it is expected to have a signal peptide. SignalP (Bendtsen et al., 2004, "Improved prediction of signal peptides: SignalP 3.0" *J Mol Biol.* 340 (4):783-95) predicts a cleavage site ("//") between amino acids 19 and 20 of SEQ ID NO:4.

[SEQ ID NO: 12]
N-terminus-MKAAALSCLFGSTLAVAGA//IESRKVHQKPLARSEPFYPS . . . -C-terminus In addition, our results demonstrate that BGL1 comprises aspartic acid at position 358, glutamine at position 381, and glutamic acid at position 385, while the published sequence provides, histidine, histidine and lysine, respectively, at the corresponding positions.

Example 3

Construction of bgl1 Expression Vectors With C1 Promoters

To produce the bgl1 sequence under control of the C1 CBH1a promoter, we cloned the bgl1 genomic sequence into a vector that includes a CBH1a promoter sequence (SEQ ID NO:8, see FIG. 4; also see PCT publication WO 01/79507), 3' regulatory sequences including a CBH1a transcription terminator, and an ampicillin resistance marker. In addition, a phleomycin resistance gene cassette was cloned into the vector at 3' to the terminator. Using the SLIC cloning technique (Mamie et al., 2007, Nature Methods 4:251- 56) the DNA corresponding to the pre-protein portion of the bgl1 sequence was amplified using primers PcbhC1bgl_F and TcbhC1bgl_R1 (see TABLE 4 in Example 2, supra). The resulting product was cloned into PmII/PacI-digested vector 3' to the CBH1a promoter to create an expression vector that expressed the BGL1 protein transcript under the control of the CBH1a promoter.

Example 4

C1 Transformation Method

Protoplast preparation

C1 cells (Alp1⁻ strain) was inoculated into 100 ml growth medium in an 500 ml Erlenmeyer flask using $10^6$ spores/ml. The culture was incubated for 48 hours at 35° C., 250 rpm. To harvest the mycelium, the culture was filtered over a sterile Myracloth filter (Calbiochem) and washed with 100 ml 1700 mosmol NaCl/CaCl2 solution (0.6 M NaCl, 0.27 M CaCl2*H20). The washed mycelia was transferred into a 50 ml tube and weighed. Caylase (20 mg/gram mycelia) was dissolved in 1700 mosmol NaCl/CaCl2 and UV-sterilized for 90 sec. 3 ml of sterile Caylase solution was added into the washed mycelia containing tube and mixed. Further 15 ml of 1700 mosmol NaCl/CaCl2 solution was added into the tube and mixed. The mycelium/Caylase suspension was incubated at 30° C., 70 rpm for 2 hours. Protoplasts were harvested by filtering through a sterile Myracloth filter into a sterile 50 ml tube. 25 ml cold STC was added to the flow through and spun down at 2720 rpm for 10 min at 4° C. The pellet was resuspended in 50 ml STC (1.2 M sorbitol, 50 mM CaCl2*H2O, 35 mM NaCl, 10 mM Tris-HCl) and centrifuged again. After the washing steps the pellet was resuspended in 1 ml STC.

Transformation

Into the bottom of a 15 ml sterile tube 6 µg plasmid DNA was pipetted and 1 µl Aurintricarboxylic acid and 100 µl protoplast were added. The content was mixed and the protoplast with the DNA were incubated at room temperature for 25 min. 1.7 ml PEG4000 solution (60% PEG4000 [polyethylene glycol, average molecular weight 4000 daltons], 50 mM $CaCl_2$*H2O, 35 mM NaCl, 10 mM Tris-HCl) was added and mixed thoroughly. The solution was kept at room temperature for 20 min. The tube was filled with STC, mixed and centrifuged at 2500 rpm for 10 min at 4° C. The STC was poured off and the pellet was resuspended in the remaining STC and plated on minimal media plates. The plates were incubated for 5 days at 35° C. Colonies were restreaked and checked for the presence of the integrated plasmid. Several isolates were selected and tested for the expression of Bgl1.

Example 5

β-Glucosidase Activity Assay

A colorimetric pNPG (p-nitrophenyl-β-D-glucopyranosideybased assay was used to measure β-glucosidase activity. β-glucosidase over-expression was determined based on the activity of secreted protein relative to wild-type C1. Untransformed (e.g., wildtype) or transformed cells were grown in 96-well plates, and media was collected. The media containing secreted protein was diluted 40-fold in 50 mM Na-acetate buffer, pH 5. 20 µL of the dilute enzyme mixture containing β-glucosidase enzyme was added to 80 µL of 2 mM pNPG (Sigma-Aldrich, Inc. St. Louis, Mo.), 50 mM Na-acetate pH5. The reactions were incubated at pH 5, 50° C. for 10 min. The reaction mixture is quenched with 100 µL of 1M sodium carbonate pH 11 solution. The absorbance of the solution is measured at 405 nm to determine the conversion of pNPG to p-nitrophenol. The release of p-nitrophenol ($\epsilon=17,700$ M-1 cm-1) is measured at 405 nm to calculate β-glucosidase activity.

Example 6

Over-Expression of BGL1

The expression vector described in Example 3, having a bgl1 sequence under the control of the C1 CBH1a promoter, was cotransformed into C1 (Alp1⁻, pyr5⁻ strain) cells along with a pyr expressing plasmid. Individual transformants were selected and cultured in 96 well plates. Media was collected from the transformants and control cells and assayed for β-glucosidase activity using the pNPG assay. The pNPG activity of the transformants was compared to the untransformed control cells (described above). Activity was measured as described in Example 5. The highest level of over-expression observed was about 35-fold over-expression, with the 10 highest expressors having 30-35 fold higher expression than wild-type.

\* \* \*

While the present invention has been described with reference to the specific embodiments thereof, it should be understood by those skilled in the art that various changes can be made and equivalents can be substituted without departing from the scope of the invention. In addition, many modifications can be made to adapt a particular situation, material, composition of matter, process, process step or steps, to achieve the benefits provided by the present invention without departing from the scope of the present invention. All such modifications are intended to be within the scope of the claims appended hereto.

All publications and patent documents cited herein are incorporated herein by reference as if each such publication or document was specifically and individually indicated to be incorporated herein by reference. Citation of publications and patent documents is not intended as an indication that any such document is pertinent prior art, nor does it constitute any admission as to the contents or date of the same.

SEQUENCE LISTING

<160> NUMBER OF SEQ ID NOS: 31

<210> SEQ ID NO 1
<211> LENGTH: 2981
<212> TYPE: DNA
<213> ORGANISM: Myceliophthora thermophila

<400> SEQUENCE: 1

```
atgaaggctg ctgcgctttc ctgcctcttc ggcagtaccc ttgccgttgc aggcgccatt      60
gaatcgagaa aggtatggac gggctttcgt caaagactcg ctccccgatc aacttcccct     120
ttcatccaga ccaccccaac cctcccagtc ctgcttcgag cacgatctct tcgggcagca     180
ccccacccac atccactcag attagcggcg acaccgttga ctgttgcaat ccgcaatcga     240
catgcaactt ccagccgcag cccaatggct gctcacgctt cccgcgaaag cctcacttgc     300
tgacaatcat cgtcaggttc accagaagcc cctcgcgaga tctgaaccctt tttacccgtc     360 gccatggatg aatcccaacg ccgacggctg ggcggaggcc tatgcccagg ccaagtcctt     420
tgtctcccaa atgactctgc tagagaaggt caacttgacc acgggagtcg ggtaagtttt     480
gtcattttgt ccaggtaaca tgcaaatggt tctgctaaca ataacttacc gtagctgggg     540
ggctgagcag tgcgtcggcc aagtgggcgc gatccctcgc cttggacttc gcagtctgtg     600
catgcatgac tcccctctcg gcatccgagg agccgactac aactcagcgt tcccctctgg     660
ccagaccgtt gctgctacct gggatcgcgg tctgatgtac cgtcgcggct acgcaatggg     720
ccaggaggcc aaaggcaagg gcatcaatgt ccttctcgga ccagtcgccg gccccttgg     780 ccgcatgccc gagggcggtc gtaactggga aggcttcgct ccggatcccg tccttaccgg     840
catcggcatg tccgagacga tcaagggcat tcaggatgct ggcgtcatcg cttgtgcgaa     900
gcactttatt ggaaacgagc agggtgagta gtcaaagacg ggccgtctcg gacccgcggc     960
ttcaagctgc tgactctgct gcagagcact tcagacaggt gccagaagcc cagggatacg    1020
gttacaacat cagcgaaacc ctctcctcca acattgacga caagaccatg cacgagctct    1080
acctttggcc gtttgccgat gccgtccggg ccggcgtcgg ctctgtcatg tgctcgtacc    1140
agcaggtcaa caactcgtac gcctgccaga actcgaagct gctgaacgac ctcctcaaga    1200
acgagcttgg gtttcagggc ttcgtcatga gcgactggca ggcacagcac actggcgcag    1260
caagcgccgt ggctggtctc gatatgtcca tgccgggcga cacccagttc aacactggcg    1320
tcagtttctg gggcgccaat ctcaccctcg ccgtcctcaa cggcacagtc cctgcctacc    1380
gtctcgacga catggccatg cgcatcatgg ccgccctctt caaggtcacc aagaccaccg    1440
acctggaacc gatcaacttc tccttctgga ccgacgacac ttatggcccg atccactggg    1500
ccgccaagca gggctaccag gagattaatt ccacgttga cgtccgcgcc gaccacggca    1560
acctcatccg ggagattgcc gccaagggta cggtgctgct gaagaatacc ggctctctac    1620
ccctgaacaa gccaaagttc gtggccgtca tcggcgagga tgctgggtcg agccccaacg    1680
ggcccaacgg ctgcagcgac cgcggctgta acgaaggcac gctcgccatg gctgggatt    1740 ccggcacagc caactatccg tacctcgttt ccccgacgc gcgctccag gcccgggcca    1800 tccaggacgg cacgaggtac gagagcgtcc tgtccaacta cgccgaggaa aagacaaagg    1860
ctctggtctc gcaggccaat gcaaccgcca tcgtcttcgt caatgccgac tcaggcgagg    1920
```

```
gctacatcaa cgtggacggt aacgagggcg accgtaagaa cctgactctc tggaacaacg    1980
gtgatactct ggtcaagaac gtctcgagct ggtgcagcaa caccatcgtc gtcatccact    2040
cggtcggccc ggtcctcctg accgattggt acgacaaccc caacatcacg gccattctct    2100
gggctggtct tccgggccag gagtcgggca actccatcac cgacgtgctt tacggcaagg    2160
tcaaccccgc cgcccgctcg cccttcactt ggggcaagac ccgcgaaagc tatggcgcgg    2220
acgtcctgta caagccgaat aatggcaatg gtgcgcccca acaggacttc accgagggcg    2280
tcttcatcga ctaccgctac ttcgacaagg ttgacgatga ctcggtcatc tacgagttcg    2340
gccacggcct gagctacacc accttcgagt acagcaacat ccgcgtcgtc aagtccaacg    2400
tcagcgagta ccggcccacg acgggcacca cggcccaggc cccgacgttt ggcaacttct    2460
ccaccgacct cgaggactat ctcttcccca aggacgagtt ccctacatc taccagtaca    2520 tctacccgta cctcaacacg accgaccccc ggagggcctc ggccgatccc cactacggcc    2580
agaccgccga ggagttcctc ccgccccacg ccaccgatga cgaccccag ccgctcctcc    2640 ggtcctcggg cggaaactcc cccggcggca accgccagct gtacgacatt gtctacacaa    2700
tcacggccga catcacgaat acgggctccg ttgtaggcga ggaggtaccg cagctctacg    2760
tctcgctggg cggtcccgag gatcccaagg tgcagctgcg cgactttgac aggatgcgga    2820
tcgaacccgg cgacgagg cagttcaccg gccgcctgac gcgcagagat ctgagcaact    2880
gggacgtcac ggtgcaggac tgggtcatca gcaggtatcc caagacggca tatgttggga    2940
ggagcagccg gaagttggat ctcaagattg agcttccttg a                       2981

<210> SEQ ID NO 2
<211> LENGTH: 2613
<212> TYPE: DNA
<213> ORGANISM: Artificial Sequence
<220> FEATURE:
<223> OTHER INFORMATION: Synthetic DNA construct of cDNA sequence
      encoding Myceliophthora thermophila C1 beta-glucosidase

<400> SEQUENCE: 2
atgaaggctg ctgcgctttc ctgcctcttc ggcagtaccc ttgccgttgc aggcgccatt      60
gaatcgagaa aggttcacca gaagcccctc gcgagatctg aaccttttta cccgtcgcca     120
tggatgaatc ccaacgccga cggctgggcg gaggcctatg cccaggccaa gtcctttgtc     180
tcccaaatga ctctgctaga aaggtcaac ttgaccacgg gagtcggctg ggggctgag      240 cagtgcgtcg gccaagtggg cgcgatccct cgccttggac ttcgcagtct gtgcatgcat     300 gactccctc tcggcatccg aggagccgac tacaactcag cgttcccctc tggccagacc     360
gttgctgcta cctgggatcg cggtctgatg taccgtcgcg gctacgcaat gggccaggag     420
gccaaaggca agggcatcaa tgtccttctc ggaccagtcg ccggccccct tggccgcatg     480
cccgagggcg tcgtaactg ggaaggcttc gctccggatc ccgtccttac cggcatcggc     540
atgtccgaga cgatcaaggg cattcaggat gctggcgtca tcgcttgtgc gaagcactt     600 attggaaacg agcaggagca cttcagacag gtgccagaag cccagggata cggttacaac     660
atcagcgaaa ccctctcctc caacattgac gacaagacca tgcacgagct ctaccttgg      720 ccgtttgccg atgccgtccg ggccggcgtc ggctctgtca tgtgctcgta ccagcaggtc     780
aacaactcgt acgcctgcca gaactcgaag ctgctgaacg acctcctcaa gaacgagctt     840
gggtttcagg gcttcgtcat gagcgactgg caggcacagc acactggcgc agcaagcgcc     900
gtggctggtc tcgatatgtc catgccgggc gacacccagt tcaacactgg cgtcagtttc     960
```

```
tggggcgcca atctcaccct cgccgtcctc aacggcacag tccctgccta ccgtctcgac   1020
gacatggcca tgcgcatcat ggccgccctc ttcaaggtca ccaagaccac cgacctggaa   1080
ccgatcaact tctccttctg gaccgacgac acttatggcc cgatccactg ggccgccaag   1140
cagggctacc aggagattaa ttcccacgtt gacgtccgcg ccgaccacgg caacctcatc   1200
cgggagattg ccgccaaggg tacggtgctg ctgaagaata ccggctctct accccctgaac  1260 aagccaaagt tcgtggccgt catcggcgag atgctgggt cgagcccaa cgggcccaac     1320 ggctgcagcg accgcggctg taacgaaggc acgctcgcca tgggctgggg atccggcaca   1380
gccaactatc cgtacctcgt ttcccccgac gccgcgctcc aggcccgggc catccaggac   1440
ggcacgaggt acgagagcgt cctgtccaac tacgccgagg aaaagacaaa ggctctggtc   1500
tcgcaggcca atgcaaccgc catcgtcttc gtcaatgccg actcaggcga gggctacatc   1560
aacgtggacg gtaacgaggg cgaccgtaag aacctgactc tctggaacaa cggtgatact   1620
ctggtcaaga cgtctcgag ctggtgcagc aacaccatcg tcgtcatcca ctcggtcggc    1680
ccggtcctcc tgaccgattg gtacgacaac cccaacatca cggccattct ctgggctggt   1740
cttccgggcc aggagtcggg caactccatc accgacgtgc tttacggcaa ggtcaacccc   1800
gccgcccgct cgcccttcac ttggggcaag accgcgaaa gctatggcgc ggacgtcctg    1860
tacaagccga ataatggcaa tggtgcgccc aacaggact tcaccgaggg cgtcttcatc    1920
gactaccgct acttcgacaa ggttgacgat gactcggtca tctacgagtt cggccacggc   1980
ctgagctaca ccaccttcga gtacagcaac atccgcgtcg tcaagtccaa cgtcagcgag   2040
taccggccca cgacgggcac cacggcccag gccccgacgt ttggcaactt ctccaccgac   2100
ctcgaggact atctcttccc caaggacgag ttccccctaca tctaccagta catctacccg   2160
tacctcaaca cgaccgaccc ccggagggcc tcggccgatc cccactacgg ccagaccgcc   2220
gaggagttcc tcccgcccca cgccaccgat gacgaccccc agccgctcct ccggtcctcg   2280
ggcggaaact ccccggcgg caaccgccag ctgtacgaca ttgtctacac aatcacggcc    2340
gacatcacga atacgggctc cgttgtaggc gaggaggtac cgcagctcta cgtctcgctg   2400
ggcggtcccg aggatcccaa ggtgcagctg cgcgactttg acaggatgcg gatcgaaccc   2460
ggcgagacga ggcagttcac cggccgcctg acgcgcagag atctgagcaa ctgggacgtc   2520
acggtgcagg actgggtcat cagcaggtat cccaagacgg catatgttgg gaggagcagc   2580
cggaagttgg atctcaagat tgagcttcct tga                                2613

<210> SEQ ID NO 3
<211> LENGTH: 851
<212> TYPE: PRT
<213> ORGANISM: Myceliophthora thermophila

<400> SEQUENCE: 3

Ile Glu Ser Arg Lys Val His Gln Lys Pro Leu Ala Arg Ser Glu Pro
1               5                   10                  15

Phe Tyr Pro Ser Pro Trp Met Asn Pro Asn Ala Asp Gly Trp Ala Glu
            20                  25                  30

Ala Tyr Ala Gln Ala Lys Ser Phe Val Ser Gln Met Thr Leu Leu Glu
        35                  40                  45

Lys Val Asn Leu Thr Thr Gly Val Gly Trp Gly Ala Glu Gln Cys Val
    50                  55                  60

Gly Gln Val Gly Ala Ile Pro Arg Leu Gly Leu Arg Ser Leu Cys Met
65                  70                  75                  80
```

```
His Asp Ser Pro Leu Gly Ile Arg Gly Ala Asp Tyr Asn Ser Ala Phe
                85                  90                  95

Pro Ser Gly Gln Thr Val Ala Ala Thr Trp Asp Arg Gly Leu Met Tyr
            100                 105                 110

Arg Arg Gly Tyr Ala Met Gly Gln Glu Ala Lys Gly Lys Gly Ile Asn
            115                 120                 125

Val Leu Leu Gly Pro Val Ala Gly Pro Leu Gly Arg Met Pro Glu Gly
        130                 135                 140

Gly Arg Asn Trp Glu Gly Phe Ala Pro Asp Pro Val Leu Thr Gly Ile
145                 150                 155                 160

Gly Met Ser Glu Thr Ile Lys Gly Ile Gln Asp Ala Gly Val Ile Ala
                165                 170                 175

Cys Ala Lys His Phe Ile Gly Asn Glu Gln Glu His Phe Arg Gln Val
            180                 185                 190

Pro Glu Ala Gln Gly Tyr Gly Tyr Asn Ile Ser Glu Thr Leu Ser Ser
            195                 200                 205

Asn Ile Asp Asp Lys Thr Met His Glu Leu Tyr Leu Trp Pro Phe Ala
210                 215                 220

Asp Ala Val Arg Ala Gly Val Gly Ser Val Met Cys Ser Tyr Gln Gln
225                 230                 235                 240

Val Asn Asn Ser Tyr Ala Cys Gln Asn Ser Lys Leu Leu Asn Asp Leu
                245                 250                 255

Leu Lys Asn Glu Leu Gly Phe Gln Gly Phe Val Met Ser Asp Trp Gln
            260                 265                 270

Ala Gln His Thr Gly Ala Ala Ser Ala Val Ala Gly Leu Asp Met Ser
            275                 280                 285

Met Pro Gly Asp Thr Gln Phe Asn Thr Gly Val Ser Phe Trp Gly Ala
290                 295                 300

Asn Leu Thr Leu Ala Val Leu Asn Gly Thr Val Pro Ala Tyr Arg Leu
305                 310                 315                 320

Asp Asp Met Ala Met Arg Ile Met Ala Ala Leu Phe Lys Val Thr Lys
                325                 330                 335

Thr Thr Asp Leu Glu Pro Ile Asn Phe Ser Phe Trp Thr Asp Asp Thr
            340                 345                 350

Tyr Gly Pro Ile His Trp Ala Ala Lys Gln Gly Tyr Gln Glu Ile Asn
            355                 360                 365

Ser His Val Asp Val Arg Ala Asp His Gly Asn Leu Ile Arg Glu Ile
        370                 375                 380

Ala Ala Lys Gly Thr Val Leu Leu Lys Asn Thr Gly Ser Leu Pro Leu
385                 390                 395                 400

Asn Lys Pro Lys Phe Val Ala Val Ile Gly Glu Asp Ala Gly Ser Ser
                405                 410                 415

Pro Asn Gly Pro Asn Gly Cys Ser Asp Arg Gly Cys Asn Glu Gly Thr
            420                 425                 430

Leu Ala Met Gly Trp Gly Ser Gly Thr Ala Asn Tyr Pro Tyr Leu Val
            435                 440                 445

Ser Pro Asp Ala Ala Leu Gln Ala Arg Ala Ile Gln Asp Gly Thr Arg
450                 455                 460

Tyr Glu Ser Val Leu Ser Asn Tyr Ala Glu Glu Lys Thr Lys Ala Leu
465                 470                 475                 480

Val Ser Gln Ala Asn Ala Thr Ala Ile Val Phe Val Asn Ala Asp Ser
                485                 490                 495
```

```
Gly Glu Gly Tyr Ile Asn Val Asp Gly Asn Glu Gly Asp Arg Lys Asn
            500                 505                 510

Leu Thr Leu Trp Asn Asn Gly Asp Thr Leu Val Lys Asn Val Ser Ser
        515                 520                 525

Trp Cys Ser Asn Thr Ile Val Ile His Ser Val Gly Pro Val Leu
    530                 535                 540

Leu Thr Asp Trp Tyr Asp Asn Pro Asn Ile Thr Ala Ile Leu Trp Ala
545                 550                 555                 560

Gly Leu Pro Gly Gln Glu Ser Gly Asn Ser Ile Thr Asp Val Leu Tyr
                565                 570                 575

Gly Lys Val Asn Pro Ala Ala Arg Ser Pro Phe Thr Trp Gly Lys Thr
            580                 585                 590

Arg Glu Ser Tyr Gly Ala Asp Val Leu Tyr Lys Pro Asn Asn Gly Asn
        595                 600                 605

Gly Ala Pro Gln Gln Asp Phe Thr Glu Gly Val Phe Ile Asp Tyr Arg
    610                 615                 620

Tyr Phe Asp Lys Val Asp Asp Ser Val Ile Tyr Glu Phe Gly His
625                 630                 635                 640

Gly Leu Ser Tyr Thr Thr Phe Glu Tyr Ser Asn Ile Arg Val Val Lys
                645                 650                 655

Ser Asn Val Ser Glu Tyr Arg Pro Thr Thr Gly Thr Thr Ala Gln Ala
            660                 665                 670

Pro Thr Phe Gly Asn Phe Ser Thr Asp Leu Glu Asp Tyr Leu Phe Pro
        675                 680                 685

Lys Asp Glu Phe Pro Tyr Ile Tyr Gln Tyr Ile Tyr Pro Tyr Leu Asn
    690                 695                 700

Thr Thr Asp Pro Arg Arg Ala Ser Ala Asp Pro His Tyr Gly Gln Thr
705                 710                 715                 720

Ala Glu Glu Phe Leu Pro Pro His Ala Thr Asp Asp Pro Gln Pro
                725                 730                 735

Leu Leu Arg Ser Ser Gly Gly Asn Ser Pro Gly Gly Asn Arg Gln Leu
            740                 745                 750

Tyr Asp Ile Val Tyr Thr Ile Thr Ala Asp Ile Thr Asn Thr Gly Ser
        755                 760                 765

Val Val Gly Glu Glu Val Pro Gln Leu Tyr Val Ser Leu Gly Gly Pro
    770                 775                 780

Glu Asp Pro Lys Val Gln Leu Arg Asp Phe Asp Arg Met Arg Ile Glu
785                 790                 795                 800

Pro Gly Glu Thr Arg Gln Phe Thr Gly Arg Leu Thr Arg Arg Asp Leu
                805                 810                 815

Ser Asn Trp Asp Val Thr Val Gln Asp Trp Val Ile Ser Arg Tyr Pro
            820                 825                 830

Lys Thr Ala Tyr Val Gly Arg Ser Arg Lys Leu Asp Leu Lys Ile
        835                 840                 845

Glu Leu Pro
    850

<210> SEQ ID NO 4
<211> LENGTH: 870
<212> TYPE: PRT
<213> ORGANISM: Myceliophthora thermophila

<400> SEQUENCE: 4

Met Lys Ala Ala Ala Leu Ser Cys Leu Phe Gly Ser Thr Leu Ala Val
1               5                   10                  15
```

```
Ala Gly Ala Ile Glu Ser Arg Lys Val His Gln Lys Pro Leu Ala Arg
         20                  25                  30

Ser Glu Pro Phe Tyr Pro Ser Pro Trp Met Asn Pro Asn Ala Asp Gly
             35                  40                  45

Trp Ala Glu Ala Tyr Ala Gln Ala Lys Ser Phe Val Ser Gln Met Thr
 50                  55                  60

Leu Leu Glu Lys Val Asn Leu Thr Thr Gly Val Gly Trp Gly Ala Glu
 65                  70                  75                   80

Gln Cys Val Gly Gln Val Gly Ala Ile Pro Arg Leu Gly Leu Arg Ser
                 85                  90                  95

Leu Cys Met His Asp Ser Pro Leu Gly Ile Arg Gly Ala Asp Tyr Asn
             100                 105                 110

Ser Ala Phe Pro Ser Gly Gln Thr Val Ala Thr Trp Asp Arg Gly
             115                 120                 125

Leu Met Tyr Arg Arg Gly Tyr Ala Met Gly Gln Glu Ala Lys Gly Lys
     130                 135                 140

Gly Ile Asn Val Leu Leu Gly Pro Val Ala Gly Pro Leu Gly Arg Met
145                 150                 155                 160

Pro Glu Gly Gly Arg Asn Trp Glu Gly Phe Ala Pro Asp Pro Val Leu
                 165                 170                 175

Thr Gly Ile Gly Met Ser Glu Thr Ile Lys Gly Ile Gln Asp Ala Gly
             180                 185                 190

Val Ile Ala Cys Ala Lys His Phe Ile Gly Asn Glu Gln Glu His Phe
         195                 200                 205

Arg Gln Val Pro Glu Ala Gln Gly Tyr Gly Tyr Asn Ile Ser Glu Thr
     210                 215                 220

Leu Ser Ser Asn Ile Asp Asp Lys Thr Met His Glu Leu Tyr Leu Trp
225                 230                 235                 240

Pro Phe Ala Asp Ala Val Arg Ala Gly Val Gly Ser Val Met Cys Ser
                 245                 250                 255

Tyr Gln Gln Val Asn Asn Ser Tyr Ala Cys Gln Asn Ser Lys Leu Leu
             260                 265                 270

Asn Asp Leu Leu Lys Asn Glu Leu Gly Phe Gln Gly Phe Val Met Ser
         275                 280                 285

Asp Trp Gln Ala Gln His Thr Gly Ala Ala Ser Ala Val Ala Gly Leu
     290                 295                 300

Asp Met Ser Met Pro Gly Asp Thr Gln Phe Asn Thr Gly Val Ser Phe
305                 310                 315                 320

Trp Gly Ala Asn Leu Thr Leu Ala Val Leu Asn Gly Thr Val Pro Ala
                 325                 330                 335

Tyr Arg Leu Asp Asp Met Ala Met Arg Ile Met Ala Ala Leu Phe Lys
             340                 345                 350

Val Thr Lys Thr Thr Asp Leu Glu Pro Ile Asn Phe Ser Phe Trp Thr
         355                 360                 365

Asp Asp Thr Tyr Gly Pro Ile His Trp Ala Ala Lys Gln Gly Tyr Gln
     370                 375                 380

Glu Ile Asn Ser His Val Asp Val Arg Ala Asp His Gly Asn Leu Ile
385                 390                 395                 400

Arg Glu Ile Ala Ala Lys Gly Thr Val Leu Leu Lys Asn Thr Gly Ser
                 405                 410                 415

Leu Pro Leu Asn Lys Pro Lys Phe Val Ala Val Ile Gly Glu Asp Ala
             420                 425                 430
```

```
Gly Ser Ser Pro Asn Gly Pro Asn Gly Cys Ser Asp Arg Gly Cys Asn
            435             440             445

Glu Gly Thr Leu Ala Met Gly Trp Gly Ser Gly Thr Ala Asn Tyr Pro
450             455             460

Tyr Leu Val Ser Pro Asp Ala Ala Leu Gln Ala Arg Ala Ile Gln Asp
465             470             475             480

Gly Thr Arg Tyr Glu Ser Val Leu Ser Asn Tyr Ala Glu Glu Lys Thr
                485             490             495

Lys Ala Leu Val Ser Gln Ala Asn Ala Thr Ala Ile Val Phe Val Asn
                500             505             510

Ala Asp Ser Gly Glu Gly Tyr Ile Asn Val Asp Gly Asn Glu Gly Asp
            515             520             525

Arg Lys Asn Leu Thr Leu Trp Asn Asn Gly Asp Thr Leu Val Lys Asn
            530             535             540

Val Ser Ser Trp Cys Ser Asn Thr Ile Val Ile His Ser Val Gly
545             550             555             560

Pro Val Leu Leu Thr Asp Trp Tyr Asp Asn Pro Asn Ile Thr Ala Ile
                565             570             575

Leu Trp Ala Gly Leu Pro Gly Gln Glu Ser Gly Asn Ser Ile Thr Asp
            580             585             590

Val Leu Tyr Gly Lys Val Asn Pro Ala Ala Arg Ser Pro Phe Thr Trp
            595             600             605

Gly Lys Thr Arg Glu Ser Tyr Gly Ala Asp Val Leu Tyr Lys Pro Asn
            610             615             620

Asn Gly Asn Gly Ala Pro Gln Gln Asp Phe Thr Glu Gly Val Phe Ile
625             630             635             640

Asp Tyr Arg Tyr Phe Asp Lys Val Asp Asp Ser Val Ile Tyr Glu
                645             650             655

Phe Gly His Gly Leu Ser Tyr Thr Thr Phe Glu Tyr Ser Asn Ile Arg
            660             665             670

Val Val Lys Ser Asn Val Ser Glu Tyr Arg Pro Thr Thr Gly Thr Thr
            675             680             685

Ala Gln Ala Pro Thr Phe Gly Asn Phe Ser Thr Asp Leu Glu Asp Tyr
690             695             700

Leu Phe Pro Lys Asp Glu Phe Pro Tyr Ile Tyr Gln Tyr Ile Tyr Pro
705             710             715             720

Tyr Leu Asn Thr Thr Asp Pro Arg Arg Ala Ser Ala Asp Pro His Tyr
                725             730             735

Gly Gln Thr Ala Glu Glu Phe Leu Pro Pro His Ala Thr Asp Asp Asp
            740             745             750

Pro Gln Pro Leu Leu Arg Ser Ser Gly Gly Asn Ser Pro Gly Gly Asn
            755             760             765

Arg Gln Leu Tyr Asp Ile Val Tyr Thr Ile Thr Ala Asp Ile Thr Asn
            770             775             780

Thr Gly Ser Val Val Gly Glu Glu Val Pro Gln Leu Tyr Val Ser Leu
785             790             795             800

Gly Gly Pro Glu Asp Pro Lys Val Gln Leu Arg Asp Phe Asp Arg Met
            805             810             815

Arg Ile Glu Pro Gly Glu Thr Arg Gln Phe Thr Gly Arg Leu Thr Arg
            820             825             830

Arg Asp Leu Ser Asn Trp Asp Val Thr Val Gln Asp Trp Val Ile Ser
            835             840             845

Arg Tyr Pro Lys Thr Ala Tyr Val Gly Arg Ser Ser Arg Lys Leu Asp
```

```
            850                 855                 860
Leu Lys Ile Glu Leu Pro
865                 870

<210> SEQ ID NO 5
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 5

Ile Glu Ser Arg Lys
1               5

<210> SEQ ID NO 6
<211> LENGTH: 19
<212> TYPE: PRT
<213> ORGANISM: Artificial Sequence
<220> FEATURE:
<223> OTHER INFORMATION: Synthetic peptide sequence

<400> SEQUENCE: 6

Met Lys Ala Ala Ala Leu Ser Cys Leu Phe Gly Ser Thr Leu Ala Val
1               5                   10                  15

Ala Gly Ala

<210> SEQ ID NO 7
<211> LENGTH: 24
<212> TYPE: PRT
<213> ORGANISM: Artificial Sequence
<220> FEATURE:
<223> OTHER INFORMATION: Synthetic peptide sequence

<400> SEQUENCE: 7

Met Lys Ala Ala Ala Leu Ser Cys Leu Phe Gly Ser Thr Leu Ala Val
1               5                   10                  15

Ala Gly Ala Ile Glu Ser Arg Lys
            20

<210> SEQ ID NO 8
<211> LENGTH: 1817
<212> TYPE: DNA
<213> ORGANISM: Myceliophthora thermophila

<400> SEQUENCE: 8
gagctccacc gcggtggcgg ccgcggatct tacaaaaaaa aggtatccga tttggggaac      60
gtcgatgaaa gtattgcaaa agtgacgaga gttgcgcaac taactcgctg ccgaagaagc     120
tgcggaagaa agagaacacc gaaagtggaa taacgttacg gatgtcctga cctcaaagtt     180
gaaaccagcc cttcctgctc tatttgggaa agcggcttgc ccttgaatgc gctgcactgt     240
ggcacgacta ccagtgatcg ggaggagcaa actaccctgg tccgttcctt ggtggggcgg     300
cactaggccc aacttagggt gatcggaggt cgatgccgcg gtcctcgttg gtctgggctc     360
ttctcatttc ccggttttgca ccccccgttg cacctgctga tcgcccgcca acgccgatga    420
ggttgcgccc agaccgacaa tcaccgcggc tgcattccca agtatattga agatggcacc     480
aggtacccgg ttttgcgtcc cagtcgtttg gtgccaaatt tgggagtttt tgagcctcaa     540
gatctgggga atcgacctc aacttccata caagttaaag tcgcacacac ggcgagttcc      600
acgaagagac acattttttt ctgaaggcct ctctccccgc acatcagaaa ccaccaaata     660
```

| | |
|---|---|
| ccaagactgc agaagccggg gtaagtgggc caccgggact acactaaaat gcggggagaa | 720 |
| gcgagatccg ttgcgaaggg aagggatggg gtgtgctgcg gctttctccg ctctcgtgcg | 780 |
| cctttgctt gaatctagtg tacaccaggg taggctccga aggagtatct acggcagcgc | 840 |
| tgttcgtgct gcgttgagag tcagggcgga gacgagcagg cgacaggagc ctcgcaccgg | 900 |
| cacttcggat cgcatttgcg cggagcgtca aatacgctct tctgcggtca tcagagagca | 960 |
| tcgtgaacca aggttcttcc gcagggcggc ctgggcttcg cagagtcgca ctcggcggac | 1020 |
| gccttccgtg tcacccctga taacctggct gccgcgccca gactcctcca atgaggtgtg | 1080 |
| tggttgccct cgccgaccct tcagcaacct taatcgcttc catcgcacgg ctccacgtcc | 1140 |
| tcgaacgatg ccctcagtcc gtgcccggcc gtggcaacca taacgtgaca tcgccgccca | 1200 |
| gcctactagc cgctatcgac cggttaggct tgtcaccgca gcgcccattc tccatcgggc | 1260 |
| ctctactctg atccacctca cccaccgcaa gcactagcga gcctcaccag agtgcaagcg | 1320 |
| acacgacccg cttggccctt cgtccttgac tatctcccag acctcttgcc atcttgccga | 1380 |
| cgccgccccc tttttttct cctcccctg ccggcaggtc ggtggcccca gtcccgagat | 1440 |
| ggcattgctc cgttgtccat gacgacccat cattcgatgg ctgactggca cactcgtctt | 1500 |
| gtttgagcat cgacggcccg cggcccgtct cccacggtac ggaacctcgt tgtacagtac | 1560 |
| ctctcgtaat gatacccaac accggggccg agcgctggga gggcggcgtt cccgagaagc | 1620 |
| cgggaaggcg gctggccggc tgacctttgt gacttggcga tggatgcggc catggagaat | 1680 |
| gtccgtccga agcgacgcga caattagcct ggctaccatc gatataaatt gggtgattcc | 1740 |
| cagctcttga tgggcgtgtc ttctgcctgg cagccctcgt cttcagatca agcaactgtg | 1800 |
| tgctgatcct cttccgt | 1817 |

<210> SEQ ID NO 9
<211> LENGTH: 2556
<212> TYPE: DNA
<213> ORGANISM: Artificial Sequence
<220> FEATURE:
<223> OTHER INFORMATION: Synthetic DNA construct of artificial polynucleotide encoding C1 BGL1 protein which is codon optimized for expression in S. cerevisiae

<400> SEQUENCE: 9

| | |
|---|---|
| atagaaagta gaaaggtaca tcaaaaacca ttagctagat cagaaccatt ctacccttct | 60 |
| ccatggatga accctaatgc agatggatgg gcagaagcat atgctcaggc caagagtttt | 120 |
| gtctcccaga tgactctgtt ggaaaaggtt aatctgacaa caggagtagg atgggggtgca | 180 |
| gaacagtgtg tcggccaagt tggtgctatc cctagattgg gtcttagaag tttgtgtatg | 240 |
| cacgattctc ccttaggtat aagaggcgct gactataact cagcattccc atccgggcaa | 300 |
| actgttgctg cgacatggga caggggtttg atgtatagaa ggggttatgc gatgggtcaa | 360 |
| gaggcaaagg gtaaaggaat taatgtattg ttggggccgg tggcggggcc actgggaaga | 420 |
| atgccagaag gtggaaggaa ctgggaagga ttcgcccccg acccagtgct aacaggtata | 480 |
| ggtatgtccg aaacgatcaa aggcatacaa gatgcaggtg ttatcgcctg tgcgaagcat | 540 |
| tttattggta tgaacaaga gcattttcgt caagtgccag aggctcaagg ttatggttat | 600 |
| aatatttctg aaactttaag ttccaacatc gatgacaaaa ccatgcacga gttatactta | 660 |
| tggccttttg cagacgctgt gagagctggc gttggctctg ttatgtgctc ttatcagcaa | 720 |
| gttaataact cttacgcctg tcaaaattcc aagttactaa atgacttatt gaagaacgaa | 780 |
| ctaggattcc aaggattcgt catgagcgat tggcaagcac agcatactgg tgctgcatcc | 840 |

```
gctgtggcag gattagatat gtcaatgcca ggagatacac aatttaatac tggcgttagt    900 tttttggggtg caaacctaac tttagctgtt ctaaacggta cggtacctgc atatcgttta    960
gacgacatgg ccatgcgtat aatggctgct ttattcaaag ttacaaaaac caccgattta   1020
gaaccaatta attttagttt ttggacagat gacacatatg gtcctataca ctgggctgct   1080
aagcaagggt accaagaaat aaatagtcac gttgacgtaa gagcggatca cggcaatctt   1140
atcagagaga tagcagcaaa gggaactgta ttgttgaaga atactggttc attaccacta   1200
aacaaaccaa gtttgtcgc agtcattggt gaagatgctg gttcatcccc taatggacca   1260
aatggttgta gtgacagagg ctgcaatgaa ggcacgttgg caatgggctg gggctcaggg   1320
actgccaatt acccctattt ggtctctccg gatgcggctt acaggctag agcaatccag   1380 gatggtacta gatacgagag cgtcctaagt aactatgccg aagaaaagac taaggcctta   1440
gtcagtcaag ccaatgccac tgctatcgtt ttcgtaaacg cggattctgg cgaaggttat   1500
atcaatgttg atggtaatga aggtgacaga agaatttaa ctttatggaa taacggcgac   1560
acattagtta aaaatgtatc aagttggtgt tccaatacta tcgtcgtgat acattctgtt   1620
ggtccagttt tactgacaga ctggtacgat aacccaaaca ttaccgccat tttatgggca   1680
ggtctgccag ggcaggaatc aggaaattcc attacggacg tactatacgg aaaggttaac   1740
ccagccgcca ggagcccttt cacatggggt aagacaagag agagctacgg agctgatgtt   1800
ctttataaac cgaacaacgg gaatggagcg ccacagcaag attttactga aggtgtgttc   1860
attgactata gatacttcga caaagttgac gatgactcag ttatatatga attcggtcac   1920
ggtctatctt atactacttt tgaatattca aatataagag tagtcaaaag taatgtttct   1980
gaatataggc cgaccaccgg aacgacggct caagcgccta ccttcggtaa tttttcaacg   2040
gatttagaag attatttatt tcccaaagac gaatttccat acatctacca atacatatac   2100
ccctatctga atactaccga tccaagaaga gcttctgccg atccacatta cgggcagact   2160
gccgaagagt tcttgccacc acacgctact gacgacgatc ctcaacctct tctgaggtcc   2220
agtggcggaa attcacctgg tggtaatagg cagctgtatg atattgtgta tactataacg   2280
gctgatatta ctaatactgg tagcgttgtt ggtgaagaag tgccgcaatt atatgtgtct   2340
ttaggtggtc cggaagatcc taaggttcag ttaagagact tgataggat gagaatagaa   2400 cctggagaaa ctaggcaatt tacaggtaga ttgacccgta gggatctgtc aaactgggat   2460
gtaacagtgc aagattgggt aatcagcagg tacccgaaaa ctgcatacgt gggtagatct   2520
tcccgtaagt tagatttgaa aattgaattg ccataa                             2556
```

<210> SEQ ID NO 10
<211> LENGTH: 60
<212> TYPE: DNA
<213> ORGANISM: Artificial Sequence
<220> FEATURE:
<223> OTHER INFORMATION: Synthetic DNA construct of sequence of primer
      PcbhClbgl_F

<400> SEQUENCE: 10

```
gtcttcagat caagcaactg tgtgctgatc ctcttccgtc atgaaggctg ctgcgctttc     60
```

<210> SEQ ID NO 11
<211> LENGTH: 18
<212> TYPE: PRT
<213> ORGANISM: Artificial Sequence
<220> FEATURE:
<223> OTHER INFORMATION: Synthetic peptide sequence

<400> SEQUENCE: 11

Met Gln Leu Pro Ala Ala Ala Gln Trp Leu Leu Thr Pro Ala Lys Ala
1               5                   10                  15

Ser Leu

<210> SEQ ID NO 12
<211> LENGTH: 39
<212> TYPE: PRT
<213> ORGANISM: Artificial Sequence
<220> FEATURE:
<223> OTHER INFORMATION: Synthetic peptide sequence of signal peptide of
      C1 BGL1

<400> SEQUENCE: 12

Met Lys Ala Ala Ala Leu Ser Cys Leu Phe Gly Ser Thr Leu Ala Val
1               5                   10                  15

Ala Gly Ala Ile Glu Ser Arg Lys Val His Gln Lys Pro Leu Ala Arg
            20                  25                  30

Ser Glu Pro Phe Tyr Pro Ser
        35

<210> SEQ ID NO 13
<211> LENGTH: 83
<212> TYPE: DNA
<213> ORGANISM: Artificial Sequence
<220> FEATURE:
<223> OTHER INFORMATION: Synthetic DNA construct

<400> SEQUENCE: 13
cggtgccatc aatcatctcg gttcgccgca gctgcttctt tctgtgcagt gaacgctctc    60
aaactgcaac gacgctgtcc gac                                            83

<210> SEQ ID NO 14
<211> LENGTH: 60
<212> TYPE: DNA
<213> ORGANISM: Artificial Sequence
<220> FEATURE:
<223> OTHER INFORMATION: Synthetic DNA construct

<400> SEQUENCE: 14
cggtgccatc aatcatctcg gttcgccgca gctgcttctt tctgtgcagt gaacgctctc    60

<210> SEQ ID NO 15
<211> LENGTH: 43
<212> TYPE: DNA
<213> ORGANISM: Artificial Sequence
<220> FEATURE:
<223> OTHER INFORMATION: Synthetic DNA construct

<400> SEQUENCE: 15
tctgtgcagt gaacgctctc aaactgcaac gacgctgtcc gac                      43

<210> SEQ ID NO 16
<211> LENGTH: 40
<212> TYPE: DNA
<213> ORGANISM: Artificial Sequence
<220> FEATURE:
<223> OTHER INFORMATION: Synthetic DNA construct

<400> SEQUENCE: 16
aatcatctcg gttcgccgca gctgcttctt tctgtgcagt                          40

-continued

<210> SEQ ID NO 17
<211> LENGTH: 30
<212> TYPE: DNA
<213> ORGANISM: Artificial Sequence
<220> FEATURE:
<223> OTHER INFORMATION: Synthetic DNA construct

<400> SEQUENCE: 17
aatcatctcg gttcgccgca gctgcttctt                                    30

<210> SEQ ID NO 18
<211> LENGTH: 250
<212> TYPE: DNA
<213> ORGANISM: Artificial Sequence
<220> FEATURE:
<223> OTHER INFORMATION: Synthetic DNA construct of sequence of intron 1
      from gene bgl1 for C1 beta-glucosidase
<220> FEATURE:
<221> NAME/KEY: Intron
<222> LOCATION: (1)..(250)
<223> OTHER INFORMATION: Intron 1 of C1 bgl1

<400> SEQUENCE: 18
aggtatggac gggctttcgt caaagactcg ctccccgatc aacttcccct ttcatccaga    60
ccaccccaac cctcccagtc ctgcttcgag cacgatctct tcgggcagca ccccacccac   120
atccactcag attagcggcg acaccgttga ctgttgcaat ccgcaatcga catgcaactt   180
ccagccgcag cccaatggct gctcacgctt cccgcgaaag cctcacttgc tgacaatcat   240
cgtcaggttc                                                         250

<210> SEQ ID NO 19
<211> LENGTH: 73
<212> TYPE: DNA
<213> ORGANISM: Artificial Sequence
<220> FEATURE:
<223> OTHER INFORMATION: Synthetic DNA construct

<400> SEQUENCE: 19
atgcaacttc cagccgcagc ccaatggctg ctcacgcttc cgcgaaagc ctcacttgct    60 gacaatcatc gtc                                                      73

<210> SEQ ID NO 20
<211> LENGTH: 70
<212> TYPE: DNA
<213> ORGANISM: Artificial Sequence
<220> FEATURE:
<223> OTHER INFORMATION: Synthetic DNA construct
<220> FEATURE:
<221> NAME/KEY: exon
<222> LOCATION: (1)..(70)
<223> OTHER INFORMATION: First exon of C1 beta-glucosidase

<400> SEQUENCE: 20 atg aag gct gct gcg ctt tcc tgc ctc ttc ggc agt acc ctt gcc gtt    48
Met Lys Ala Ala Ala Leu Ser Cys Leu Phe Gly Ser Thr Leu Ala Val
1               5                   10                  15 gca ggc gcc att gaa tcg aga a                                       70
Ala Gly Ala Ile Glu Ser Arg
            20

<210> SEQ ID NO 21
<211> LENGTH: 240
<212> TYPE: DNA
<213> ORGANISM: Artificial Sequence
<220> FEATURE:
<223> OTHER INFORMATION: Synthetic DNA construct

<400> SEQUENCE: 21

```
atgaaggctg ctgcgctttc ctgcctcttc ggcagtaccc ttgccgttgc aggcgccatt    60
gaatcgagaa aggtatggac cacgatctct tcgggcagca ccccacccac atccactcag   120
attagcggcg acaccgttga ctgttgcaat ccgcaatcga catgcaactt ccagccgcag   180
cccaatggct gctcacgctt cccgcgaaag cctcacttgc tgacaatcat cgtcaggttc   240
```

<210> SEQ ID NO 22
<211> LENGTH: 20
<212> TYPE: DNA
<213> ORGANISM: Artificial Sequence
<220> FEATURE:
<223> OTHER INFORMATION: Synthetic DNA construct of sequence of internal
      primer C1bg1_fwd1

<400> SEQUENCE: 22

```
atgaaggctg ctgcgctttc                                                20
```

<210> SEQ ID NO 23
<211> LENGTH: 27
<212> TYPE: DNA
<213> ORGANISM: Artificial Sequence
<220> FEATURE:
<223> OTHER INFORMATION: Synthetic DNA construct of sequence of internal
      primer C1bg1_rev1

<400> SEQUENCE: 23

```
tcattaagga agctcaatct tgagatc                                        27
```

<210> SEQ ID NO 24
<211> LENGTH: 25
<212> TYPE: DNA
<213> ORGANISM: Artificial Sequence
<220> FEATURE:
<223> OTHER INFORMATION: Synthetic DNA construct of sequence of external
      primer C1bg1_fwd2

<400> SEQUENCE: 24

```
tctctgccgg tgccatcaat catct                                          25
```

<210> SEQ ID NO 25
<211> LENGTH: 24
<212> TYPE: DNA
<213> ORGANISM: Artificial Sequence
<220> FEATURE:
<223> OTHER INFORMATION: Synthetic DNA construct of sequence of external
      primer C1bg1_rev2

<400> SEQUENCE: 25

```
gctcaccgga acttgccaag tgct                                           24
```

<210> SEQ ID NO 26
<211> LENGTH: 29
<212> TYPE: DNA
<213> ORGANISM: Artificial Sequence
<220> FEATURE:
<223> OTHER INFORMATION: Synthetic DNA construct of sequence of primer
      cdx09050

<400> SEQUENCE: 26

```
ggctcatgaa ggctgctgcg ctttcctgc                                      29
```

<210> SEQ ID NO 27
<211> LENGTH: 34

```
<212> TYPE: DNA
<213> ORGANISM: Artificial Sequence
<220> FEATURE:
<223> OTHER INFORMATION: Synthetic DNA construct of sequence of primer
      cdx09052

<400> SEQUENCE: 27
gccgaattct caaggaagct caatcttgag atcc                                    34

<210> SEQ ID NO 28
<211> LENGTH: 60
<212> TYPE: DNA
<213> ORGANISM: Artificial Sequence
<220> FEATURE:
<223> OTHER INFORMATION: Synthetic DNA construct of sequence of primer
      TcbhC1bgl_R1

<400> SEQUENCE: 28
gtcttcagat caagcaactg tgtgctgatc ctcttccgtc atgaaggctg ctgcgctttc         60

<210> SEQ ID NO 29
<211> LENGTH: 4
<212> TYPE: PRT
<213> ORGANISM: Artificial Sequence
<220> FEATURE:
<223> OTHER INFORMATION: Synthetic peptide sequence

<400> SEQUENCE: 29

Glu Ser Arg Lys
1

<210> SEQ ID NO 30
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 30

Ala Asp Asn His Arg Gln
1               5

<210> SEQ ID NO 31
<211> LENGTH: 24
<212> TYPE: PRT
<213> ORGANISM: Artificial Sequence
<220> FEATURE:
<223> OTHER INFORMATION: Synthetic peptide sequence

<400> SEQUENCE: 31

Met Gln Leu Pro Ala Ala Ala Gln Trp Leu Leu Thr Pro Ala Lys Ala
1               5                   10                  15

Ser Leu Ala Asp Asn His Arg Gln
            20
```

We claim:

1. An isolated polynucleotide encoding a recombinant β-glucosidase polypeptide, wherein said isolated polynucleotide comprises SEQ ID NO:9.

2. An expression vector comprising the polynucleotide of claim 1, operably linked to a heterologous promoter.

3. The expression vector of claim 2, wherein the heterologous promoter is the *M. thermophile* C1 cellobiohydrolase 1a (CBH1a) promoter.

4. A method of producing a β-glucosidase polypeptide, comprising culturing a cell comprising the polynucleotide according to claim 1, operably linked to a heterologous promoter, under conditions in which β-glucosidase is produced.

5. The method of claim 4, wherein the cell is *Myceliophthora thermophila* cell.

6. The method of claim 4, wherein the heterologous promoter is the *M. thermophila* C1 cellobiohydrolase 1a (CBH1a) promoter.

7. The method of claim 4, further comprising recovering the β-glucosidase produced by the cell.

8. A method of producing a β-glucosidase polypeptide, comprising culturing a cell comprising the expression vector according to claim 2, under conditions in which β-glucosidase is produced.

9. The method of claim 8, wherein the heterologous promoter is the *M. thermophila* C1 cellobiohydrolase 1a (CBH1a) promoter.

10. The method of claim 8, wherein the cell is *Myceliophthora thermophila* cell.

11. The method of claim 8, further comprising recovering the β-glucosidase produced by the cell.

12. A recombinant host cell comprising the polynucleotide according to claim 1, encoding a recombinant β-glucosidase polypeptide, wherein the encoding sequence does not comprise introns, and wherein optionally the polynucleotide is operably linked to a heterologous promoter.

13. The recombinant host cell of claim 12, wherein the cell expresses at least one other recombinant cellulase enzyme.

14. The recombinant host cell of claim 12, wherein the cell is *Myceliophthora thermophila* cell.

15. The recombinant host cell of claim 12, wherein the heterologous promoter is the *M. thermophila* C1 cellobiohydrolase 1a (CBH1a) promoter.

* * * * *